(12) United States Patent
Ohno et al.

(10) Patent No.: US 7,442,516 B2
(45) Date of Patent: Oct. 28, 2008

(54) ANTIBODY SPECIFIC TO CENTRAL NERVOUS SYSTEM TAU PROTEIN

(75) Inventors: Hideto Ohno, Tokyo (JP); Koichi Ishiguro, Machida (JP); Masaki Imagawa, Osaka (JP)

(73) Assignees: Mitsubishi Chemical Corporation, Tokyo (JP); Mitsubishi Kagaku Iatron, Inc., Tokyo (JP)

( * ) Notice: Subject to any disclaimer, the term of this patent is extended or adjusted under 35 U.S.C. 154(b) by 0 days.

(21) Appl. No.: 11/055,747

(22) Filed: Feb. 11, 2005

(65) Prior Publication Data

US 2005/0181460 A1 Aug. 18, 2005

Related U.S. Application Data

(63) Continuation of application No. PCT/JP03/10340, filed on Aug. 14, 2003.

(30) Foreign Application Priority Data

Aug. 14, 2002 (JP) .................. 2002-236472

(51) Int. Cl.
| | |
|---|---|
| C07K 16/18 | (2006.01) |
| G01N 33/53 | (2006.01) |
| G01N 33/531 | (2006.01) |
| G01N 33/543 | (2006.01) |
| G01N 33/567 | (2006.01) |
| C12P 21/08 | (2006.01) |
| G01N 33/536 | (2006.01) |
| G01N 33/537 | (2006.01) |
| G01N 33/577 | (2006.01) |

(52) U.S. Cl. .............. 435/7.21; 435/7.1; 435/7.92; 435/7.93; 435/7.94; 435/7.95; 435/962; 435/975; 436/503; 436/518; 436/536; 436/547; 436/63; 436/174; 436/175; 530/388.2; 530/389.1

(58) Field of Classification Search ............ 435/7.1, 435/7.21, 7.92–7.95, 962, 975; 436/503, 436/518, 536, 547, 63, 174, 175; 530/388.2, 530/389.1

See application file for complete search history.

(56) References Cited

U.S. PATENT DOCUMENTS

| | | | |
|---|---|---|---|
| 5,492,812 A | 2/1996 | Vooheis | |
| 6,136,963 A * | 10/2000 | Chandrashekar | 536/23.1 |
| 6,500,674 B1 * | 12/2002 | Vandermeeren et al. | 436/518 |
| 6,589,746 B1 * | 7/2003 | Zemlan | 435/7.1 |
| 6,680,173 B2 * | 1/2004 | Vanmechelen et al. | 435/7.1 |
| 2002/0086009 A1 | 7/2002 | Ishiguro et al. | |

FOREIGN PATENT DOCUMENTS

| | | |
|---|---|---|
| JP | 2002-40023 | 2/2002 |
| WO | 96/04309 | 2/1996 |
| WO | 97/34145 | 9/1997 |
| WO | 00/14546 | 3/2000 |

OTHER PUBLICATIONS

Gu, Yongjun et al., "τ Is Widely Expressed in Rat Tissues", Journal of Neurochemistry 67(3), 1235-1244, (1996).
Goedert, M., et al. "Multiple Isoforms of Human Microtubule-Associated Protein Tau: Sequences and Localization in Neurofibrillary Tangles of Alzheimer's Disease", Neuron 3, 519-526 (1989).
Grundke-Iqbal et al., "Abnormal phosphorylation of the microtubule-associated protein τ(tau) in Alzheimer cytoskeletal pathology", Proc. Natl. Acad. Sci. USA, vol. 83, No. 13, pp. 4913-4717,Jul. 1986.
Mercken et al., "Monoclonal Antibodies with Selective Specificity for Alzheimer Tau are Directed Against Phosphatase-Sensitive Epitopes", *Acto. Neuropthol.*, vol. 84, pp. 265-272, 1992.
Tranchant, "Tau Proteins and Neurodegenerative Diseases", *M/S Medecine Sciences Societe des Periodiques Flammarion*, vol. 13, No. 8-9, 1997. (Translation of relevant passage on p. 992).
Biernat et al., "The Switch of Tau Protein to an Alzheimer-Like State includes the Phosphorylation of Two Serine—Proline Motifs Upstream of the Microtubule Binding Region", *Embo. Journal*, vol. 11, No. 4, pp. 1593-1597, 1992.

* cited by examiner

*Primary Examiner*—Mark L Shibuya
*Assistant Examiner*—James L Grun
(74) *Attorney, Agent, or Firm*—Wenderoth, Lind & Ponack, L.L.P.

(57) ABSTRACT

The present invention provides an antibody which specifically recognizes a CNS tau protein but not a peripheral tau protein. More specifically, the present invention provides an antibody obtainable by using a polypeptide comprising an amino acid sequence of a connective portion between the amino acid sequence encoded by Exon 4 of a gene encoding a tau protein and the amino acid sequence encoded by Exon 5 thereof as an epitope specific to the isoform of tau protein predominantly existing in central nervous tissues. The present invention further provides a method of detecting Alzheimer's disease and a reagent kit using the antibody.

12 Claims, 2 Drawing Sheets

SEQUENCE LISTING

```
<160> NUMBER OF SEQ ID NOS: 9

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Glu Ser Pro Leu
         35                  40                  45

Gln Thr Pro Thr Glu Asp Gly Ser Glu Glu Pro Gly Ser Glu Thr Ser
     50                  55                  60

Asp Ala Lys Ser Thr Pro Thr Ala Glu Asp Val Thr Ala Pro Leu Val
 65                  70                  75                  80
```

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 2
<211> LENGTH: 250
<212> TYPE: PRT
<213> ORGANISM: Homo sapiens

<400> SEQUENCE: 2

Pro Glu Ser Gly Lys Val Val Gln Glu Gly Phe Leu Arg Glu Pro Gly
 1               5                  10                  15

```
Pro Pro Gly Leu Ser His Gln Leu Met Ser Gly Met Pro Gly Ala Pro
             20                  25                  30

Leu Leu Pro Glu Gly Pro Arg Glu Ala Thr Arg Gln Pro Ser Gly Thr
         35                  40                  45

Gly Pro Glu Asp Thr Glu Gly Arg His Ala Pro Glu Leu Leu Lys
     50                  55                  60

His Gln Leu Leu Gly Asp Leu His Gln Glu Gly Pro Pro Leu Lys Gly
 65                  70                  75                  80

Ala Gly Gly Lys Glu Arg Pro Gly Ser Lys Glu Glu Val Asp Glu Asp
                 85                  90                  95

Arg Asp Val Asp Glu Ser Ser Pro Gln Asp Ser Pro Ser Lys Ala
            100                 105                 110

Ser Pro Ala Gln Asp Gly Arg Pro Pro Gln Thr Ala Ala Arg Glu Ala
            115                 120                 125

Thr Ser Ile Pro Gly Phe Pro Ala Glu Gly Ala Ile Pro Leu Pro Val
    130                 135                 140

Asp Phe Leu Ser Lys Val Ser Thr Glu Ile Pro Ala Ser Glu Pro Asp
145                 150                 155                 160

Gly Pro Ser Val Gly Arg Ala Lys Gly Gln Asp Ala Pro Leu Glu Phe
                165                 170                 175

Thr Phe His Val Glu Ile Thr Pro Asn Val Gln Lys Glu Gln Ala His
            180                 185                 190

Ser Glu Glu His Leu Gly Arg Ala Ala Phe Pro Gly Ala Pro Gly Glu
                195                 200                 205

Gly Pro Glu Ala Arg Gly Pro Ser Leu Gly Glu Asp Thr Lys Glu Ala
    210                 215                 220

Asp Leu Pro Glu Pro Ser Glu Lys Gln Pro Ala Ala Ala Pro Arg Gly
225                 230                 235                 240

Lys Pro Val Ser Arg Val Pro Gln Leu Lys
                245                 250

<210> SEQ ID NO 3
<211> LENGTH: 14
<212> TYPE: PRT
<213> ORGANISM: Homo sapiens

<400> SEQUENCE: 3

Ala Ala Gly His Val Thr Gln Ala Arg Met Val Ser Lys Ser
 1               5                  10

<210> SEQ ID NO 4
<211> LENGTH: 8
<212> TYPE: PRT
<213> ORGANISM: Homo sapiens

<400> SEQUENCE: 4

His Val Thr Gln Ala Arg Met Val
 1               5

<210> SEQ ID NO 5
<211> LENGTH: 9
<212> TYPE: PRT
<213> ORGANISM: Homo sapiens

<400> SEQUENCE: 5

His Val Thr Gln Ala Arg Met Val Ser
 1               5
```

```
<210> SEQ ID NO 6
<211> LENGTH: 15
<212> TYPE: PRT
<213> ORGANISM: Homo sapiens

<400> SEQUENCE: 6

Ala Ala Pro Arg Gly Lys Pro Val Ser Arg Val Pro Gln Leu Lys
 1               5                  10                  15

<210> SEQ ID NO 7
<211> LENGTH: 191
<212> TYPE: PRT
<213> ORGANISM: Homo sapiens

<400> SEQUENCE: 7

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Ala Glu Glu Ala
         35                  40                  45

Gly Ile Gly Asp Thr Pro Ser Leu Glu Asp Glu Ala Ala Gly His Val
     50                  55                  60

Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                 85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro
            180                 185                 190

<210> SEQ ID NO 8
<211> LENGTH: 13
<212> TYPE: PRT
<213> ORGANISM: Homo sapiens

<400> SEQUENCE: 8

Lys Asp Gln Gly Gly Tyr Thr Met His Gln Asp Gln Glu
 1               5                  10

<210> SEQ ID NO 9
<211> LENGTH: 11
<212> TYPE: PRT
<213> ORGANISM: Homo sapiens

<400> SEQUENCE: 9

Gly Thr Gly Ser Asp Asp Lys Lys Ala Lys Gly
 1               5                  10
```

US 7,442,516 B2

ANTIBODY SPECIFIC TO CENTRAL NERVOUS SYSTEM TAU PROTEIN

This application is a continuation of International Application No. PCT/JP03/10340 filed Aug. 14, 2003.

TECHNICAL FIELD

The present invention relates to an antibody that specifically recognizes tau protein of central nervous system (CNS tau protein) but not tau protein of peripheral tissue (peripheral tau protein). In addition, the present invention relates to a method of detecting tauopathy in which the presence of the CNS tau protein in a sample is analyzed, particularly to a method of detecting Alzheimer's disease, and also to a reagent kit.

BACKGROUND ART

Alzheimer's disease is progressive dementia occurring at the presenile stage (between the ages of 45 and 65). It causes morbid changes such as degeneration of neurons and atrophy of cerebral cortex due to a decrease in the number of neurons. Pathologically, a number of senile plaques and neurofibrillary degeneration are observed in the brain. So-called senile dementia caused by spontaneous aging in the senium at the age of 65 or older is not substantially different from Alzheimer's disease from the pathological viewpoint and is regarded as senile dementia of the Alzheimer type. This disease has been perceived as a social problem because the number of patients suffering from Alzheimer's disease increases as the senile population increases. Although there are various hypotheses about the causes of this disease, it remains to be elucidated and an early breakthrough in clarification of the disease is desired.

The main component of senile plaques that is one of the pathological changes caused by Alzheimer's disease is known to be amyloid β protein (Annu. Rev. Neurosci., 12, 463-490 (1989)). Neurofibrillary degeneration that is another pathological change shows accumulation of the paired helical filament (may hereinafter be referred to as PHF) in neurons and phosphorylated tau protein is identified as one of its constituents (J. Biochem. 99, 1807-1810 (1986); Proc. Natl. Acad. Sci. USA, 83, 4913-4917 (1986)).

Although tau protein is composed of a group of protein isoforms that usually form several bands at a molecular weight of 48 to 65 kD (as a result of SDS-polyacrylamide gel electrophoresis) and promotes formation of microtubules, tau protein incorporated in the PHF of the Alzheimer diseased brain has been proven to be abnormally phosphorylated as compared with that in the normal brain using a polyclonal antibody to PHF (anti-p-tau; J. Biochem., 99, 1807-1810 (1986)) and a monoclonal antibody to tau protein (tau-1 antibody; Proc. Natl. Acad. Sci. USA, 83, 4913-4917 (1986)). Further, the phosphorylation sites of phosphorylated tau protein incorporated in the PHF have been identified (JP 6-239893 A), and functions of tau protein involved in Alzheimer's disease is now being clarified.

For tau proteins, a kit for measuring the concentration of a tau protein in cerebrospinal fluid (trade name in Japan "Finoscolor hTAU" and trade name in the U.S. and Europe "INNOTEST hTAU Ag", manufactured by Innogenetics) has been already commercially available and clinically utilized. A method of detecting Alzheimer's disease based on the phosphorylation site of a phosphorylated tau protein in PHF has been developed (Neurosci. Lett., 270, 91-94 (1999); Ann. Neurol., 50, 150-156 (2001)). Both of those methods are designed to use cerebrospinal fluid as a sample. The collection of the samples is problematic for patients due to its highly invasive nature. Thus, in light of in the need to reduce invasiveness for patients and convenient analysis, there have been strong demands for specific and sensitive methods of detecting Alzheimer's disease in which a CNS tau protein can be analyzed even by using a variety of samples not limited to cerebrospinal fluid and including blood.

However, it has been revealed that several different isoforms exist for the tau protein. A central nervous tissue, such as the brain, and a peripheral tissue, such as the muscle, have different isoforms of the tau protein which predominantly exist in each tissue (J. Neurochem., 67, 1235-1244 (1996)). For example, the isoform of a tau protein that predominantly exists in a peripheral tissue (hereinafter, which is also referred to as a "peripheral tau protein") has a large molecular weight as compared to the isoform of a tau protein that predominantly exists in a central nervous tissue (hereinafter, which is also referred to as a "CNS tau protein"). It has been suggested that, in a blood sample or the like, this peripheral tau protein having a large molecular weight is contained in a large amount.

The inventors of the present invention have previously proposed a method of detecting Alzheimer's disease using blood as a sample (JP 2002-040023 A). However, in this method, the different isoforms of a tau protein are not distinguished, and thereby all are detected. Therefore, the method does not allow one to specifically analyze a change in the CNS tau protein that occurs in the brain of a patient with Alzheimer's disease. For example, when a blood sample or the like is analyzed using such a method, the detection of a CNS tau protein is interfered with by the strong reaction of a peripheral tau protein having a large molecular weight that is also contained in a large amount in the blood sample. As a result, sufficient sensitivity was not obtained.

In short, it has been difficult to analyze a tau protein derived from a central nervous tissue whose content is low in a blood sample, or the like in which extremely high concentrations of gross proteins are present resulting in a large interference due to impurities (Dement. Geriat. Cong. Disord., 10, 442-445 (1999); Neurosci. Lett., 275, 159-162 (1999)). Thus, the establishment of specific and sensitive methods of detecting Alzheimer's disease has not been established.

In addition, mild cognitive impairment (hereinafter, which may be abbreviated to "MCI") showing a subjective symptom of memory loss or the like has recently received attention as prodrome of Alzheimer's disease. Of patients diagnosed as having MCI, 10-15% in a year and 50% in several years have been said to proceed to Alzheimer's disease, and there is a growing acknowledgement that patients with early Alzheimer's disease are included in MCI patients. However, existing evaluation for MCI complies with a criterion such as the criteria of Petersen, R. C. et al., (Arch. Neurol., 56, 303-308 (1999)) that focuses on history taking or intelligent function examinations. Thus, objective and clear diagnostics have not been established. Furthermore, those conventional methods are unable to detect patients with early Alzheimer's disease among a group of patients diagnosed as having MCI. Consequently, there is a strong demand to establish methods of distinctly detecting Alzheimer's disease for patients including such patients diagnosed as having MCI.

DISCLOSURE OF THE INVENTION

The present invention has been made to provide a highly specific, sensitive, and convenient method of detecting Alzheimer's disease.

The inventors of the present invention have devoted themselves to extensive studies for attaining the above objective and found that the detection of Alzheimer's disease can be carried out specifically and conveniently by analysis using an antibody that specifically recognizes a CNS tau protein but not a peripheral tau protein. More particularly, the inventors of the present invention have found that a CNS tau protein can be reliably analyzed by employing an antibody obtainable by using an antigen of a polypeptide containing an amino acid sequence of the connective portion between the amino acid sequence encoded by Exon 4 of a gene encoding a tau protein and the amino acid sequence encoded by Exon 5, as an epitope specific to the isoform of the tau protein predominantly existing in a central nervous tissue, and that the concentration of the CNS tau protein thus analyzed significantly changed in a sample obtained from a patient with Alzheimer's disease. The present invention has been accomplished on the basis of those findings.

Namely, according to one aspect of the present invention, there are provided:

(1) An antibody specific to a CNS tau protein, wherein the antibody specifically recognizes a CNS tau protein but not a peripheral tau protein;

(2) The antibody according to (1), wherein the CNS tau protein is a protein that is specifically increased in body fluid of a patient with Alzheimer's disease;

(3) The antibody according to (1) or (2), wherein the antibody is obtained by using a polypeptide containing an amino acid sequence specific to the CNS tau protein as an antigen;

(4) The antibody according to (3), wherein the amino acid sequence specific to the CNS tau protein comprises a sequence containing an amino acid sequence of a connective portion between the amino acid sequence encoded by Exon 4 of a gene encoding a tau protein and the amino acid sequence encoded by Exon 5 thereof;

(5) The antibody according to (4), wherein the sequence containing the amino acid sequence of the connective portion is an amino acid sequence represented by amino acid numbers 121-128 of an amino acid sequence described in SEQ ID NO: 1 of the sequence listing; and (6) A method of producing an antibody specific to a CNS tau protein, comprising: immunizing an animal with a polypeptide containing an amino acid sequence specific to a CNS tau protein as an antigen; analyzing reactivity of a resulting antibody with the CNS tau protein and a peripheral tau protein; and selecting an antibody having reactivity specific to the CNS tau protein.

According to another aspect of the present invention, there are provided:

(7) A method of detecting tauopathy, comprising analyzing the presence of a CNS tau protein in a sample obtained from an individual suspected of tauopathy using the antibody according to any one of (1) to (5);

(8) The method according to (7), in which the tauopathy is Alzheimer's disease;

(9) The method according to (7) or (8), wherein the sample has been treated by denaturation in the presence of a protein-solubilizing agent to remove concomitant proteins;

(10) The method according to (9), wherein the sample has been further treated by condensation;

(11) The method according to any one of (7) to (10), wherein the sample is blood; and

(12) The method according to any one of (7) to (11), wherein the analysis of the presence of the CNS tau protein is carried out by enzyme-linked immunosorbent assay.

According to another aspect of the present invention, there is provided:

(13) A reagent kit for detecting Alzheimer's disease, comprising at least the antibody as defined in any one of (1) to (5).

BEST MODE FOR CARRYING OUT THE INVENTION

Figure 1:
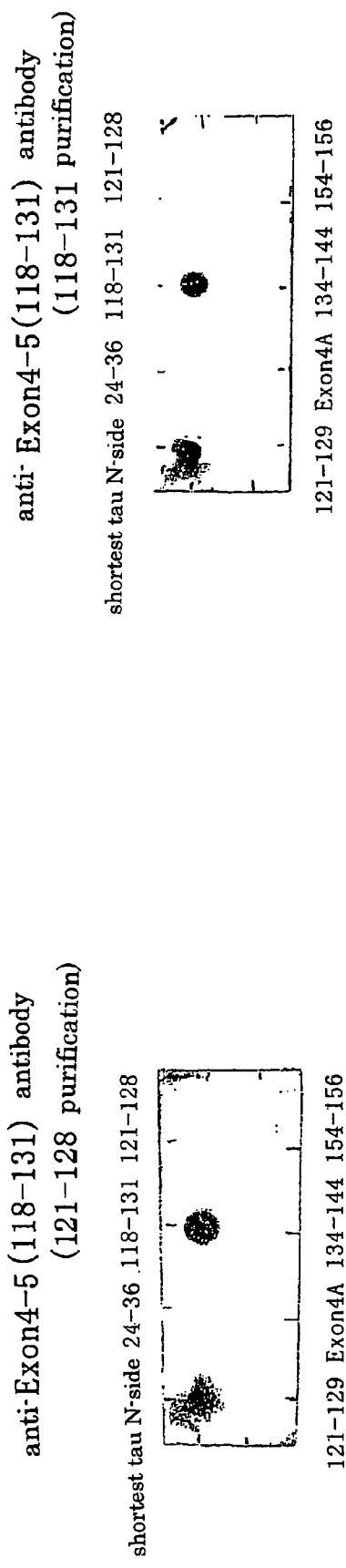
FIG. 1 is a photographic diagram showing the result of dot blot analysis carried out for analyzing the specificity of the antibody of the present invention. Each of four antibodies which have been produced is reacted with eight antigenic polypeptides dot-blotted on a PVDF membrane and is detected by color development reaction.
Figure 1:
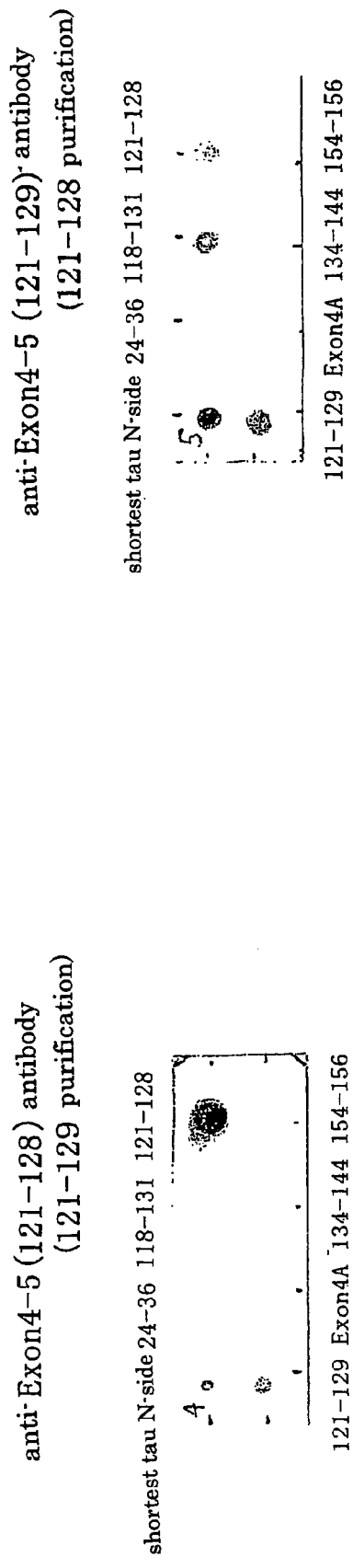

Hereinafter, the present invention will be further described in detail.

1. CNS and Peripheral Tau Proteins

A method of detecting tauopathy, especially a method of detecting Alzheimer's disease, of the present invention, is characterized by using an antibody that specifically recognizes a CNS tau protein but not a peripheral tau protein (hereinafter, which is also referred to as an "antibody specific to a CNS tau protein") to analyze the presence of the CNS tau protein in a sample obtained from an individual suspected of Alzheimer's disease.

A "CNS tau protein" as used herein means the isoform of a tau protein that predominantly exists in a central nervous tissue such as the brain and includes mainly six isoforms for human (Neuron, 3, 519-526 (1989)). Those isoforms of the CNS tau protein have a common feature of lacking an insertion sequence between the amino acid No. 124 (Gln) and No. 125 (Ala) in the amino acid sequence described in SEQ ID NO: 1 of the sequence listing. Here, "between the amino acid No. 124 and No. 125" refers to a sequence of the connective portion (GlnAla; hereinafter, which is also referred to as an "Exon 4-5 connective portion") between the amino acid sequence encoded by Exon 4 of a gene encoding a tau protein (amino acid numbers 103-124 of SEQ ID NO: 1) and the amino acid sequence encoded by Exon 5 thereof (amino acid numbers 125-143 of SEQ ID NO: 1). The sequence of a CNS tau protein shown herein (SEQ ID NO: 1) is the longest sequence of the isoform of a tau protein in a human central nervous tissue which is described in Neuron, 3, 519-526 (1989), and the amino acid numbering used herein is that of the above sequence.

"Peripheral tau protein" means the isoform of a tau protein predominantly existing in a peripheral tissue such as the muscle, and more particularly means, for example, the isoform having an insertion sequence between amino acid no. 124 and no. 125 in an amino acid sequence described in SEQ ID NO: 1 of the sequence listing. For a human being, examples of the above insertion sequence in the peripheral tau protein include an amino acid sequence encoded by Exon 4A of a gene encoding a tau protein (SEQ ID NO: 2; Biochem., 31, 10626-10633 (1992)).

Here, each of the CNS tau protein and the peripheral tau protein may or may not be a phosphorylated one, and also includes a fragment thereof.

In a central nervous tissue such as the brain of a patient with Alzheimer's disease, the above CNS tau protein is highly phosphorylated and loses its original function. This protein is then released with or without fragmentation and enters cerebrospinal fluid. The CNS tau protein sometimes flows into body fluid such as blood or lymph, because there is a transport between cerebrospinal fluid and body fluid such as blood or lymph (Nyumon Visual Science "Mechanism of Brain" by Yasumasa Arai, Nippon Jitsugyo Publishing Co., Ltd.). Especially in blood, the peripheral tau protein is contained in a large amount so that if the blood is used as a sample, it is necessary to analyze only the CNS tau protein distinguished from the peripheral tau protein. As described above, the CNS tau protein and the peripheral tau protein are distinguished from each other on the basis of the presence or absence of the insertion sequence between amino acid no. 124 and no. 125 of the sequence described in SEQ. ID. NO.: 1 of the sequence listing. Preferably, they are distinguished by using, for example, an antibody against the amino acid sequence of the Exon 4-5 connective portion as an epitope.

The deviation of the tau protein from a central nervous tissue to body fluid in a patient with Alzheimer's disease as described above may occur through similar mechanisms in patients with the other diseases having the above CNS tau protein that is highly phosphorylated in a central nervous tissue. Examples of such diseases include a group of diseases classified as tauopathy that has neurodegeneration caused by the accumulation of tau proteins in a central nervous tissue. Examples of tauopathy other than Alzheimer's disease include Down's syndrome, Parkinson's syndrome, Pick disease, progressive supranuclear palsy (PSP), and corticobasal degeneration (CBD).

2. Antibody Specific to CNS Tau Protein

In the present invention, any antibody can be used as long as it specifically recognizes a CNS tau protein but not a peripheral tau protein, and examples thereof include an antibody obtained by using, as an antigen, a polypeptide composed of an amino acid sequence specific to a CNS tau protein (hereinafter, which is also referred to as an "antigenic polypeptide"). That is, the antigenic polypeptide may have any sequence as long as an antibody obtained by immunizing an animal with the polypeptide composed of the amino acid sequence specific to a CNS tau protein can distinguish a CNS tau protein from a peripheral tau protein and can specifically recognize a CNS tau protein. In the present invention, an "amino acid sequence specific to a CNS tau protein" refers to an amino acid sequence that is present in the amino acid sequence of a CNS tau protein but not in that of a peripheral tau protein.

Examples of the amino acid sequence specific to a CNS tau protein include an amino acid sequence of the connective portion (Exon 4-5 connective portion) between an amino acid sequence encoded by Exon 4 of a gene encoding a tau protein and an amino acid sequence encoded by Exon 5 thereof (e.g., amino acid No. 124 (Gln) and No. 125 (Ala) of SEQ ID NO: 1). Preferably used as an antigenic polypeptide is, for example, a polypeptide of 5 or more amino acid residues, more preferably 8 or more residues, or most preferably 10 or more residues including the amino acid sequence of such a connective portion (amino acids of amino acid No. 124 (Gln) and No. 125 (Ala)). An upper limit to the length of the antigenic polypeptide is not particularly restricted as long as it can generate an antibody specific to a CNS tau protein. Generally, the upper limit is 20 or less, preferably 15 or less residues. A preferred sequence of the antigenic polypeptide used in the present invention contains at least the amino acid sequence (GlnAla) of the Exon 4-5 connective portion and amino acid residues added to both ends of GlnAla which are not particularly limited but preferably amino acid residues from human tau protein themselves shown in SEQ ID NO: 1. Although the position of the amino acid sequence of the Exon 4-5 connective portion is not particularly limited, it is preferred that the sequence is placed at the central portion of the polypeptide. That is, the antigenic polypeptide is preferably a polypeptide that contains 1 to 8 amino acid residues, preferably about 3 to 6 residues of the sequence of human tau protein, at both the ends of the amino acid sequence (GlnAla) of the connective portion.

Specific examples of a preferred sequence thereof include a polypeptide containing a sequence represented by the amino acid numbers 121-128 of the sequence described in SEQ ID NO: 1 of the sequence listing. Specific examples of a more preferable sequence include a polypeptide having a sequence represented by the amino acid numbers 118-131 of SEQ ID NO: 1 (SEQ ID NO: 3; hereinafter, which is also referred to as a "polypeptide 118-131"), a polypeptide having a sequence represented by amino acid numbers 121-128 of SEQ ID NO: 1 (SEQ ID NO: 4; hereinafter, which is also referred to as a "polypeptide 121-128"), and a polypeptide having a sequence represented by amino acid numbers 121-129 of SEQ ID NO: 1 (SEQ ID NO: 5; hereinafter, which is also referred to as a "polypeptide 121-129").

The antibody of the present invention may be a monoclonal antibody or a polyclonal antibody, and a polyclonal antibody is preferably used. A method of preparing an antibody can employ an ordinal method known in this art. If a polyclonal antibody, for example, is produced, the above antigenic polypeptide is bound to a carrier protein such as BSA (bovine serum albumin), porcine thyroid globulin, or KLH (keyhole limpet hemocyanin) using an appropriate condensing agent such as carbodiimide or maleimide to produce an antigen for immunization (immunogen). The binding of the antigenic polypeptide to the carrier protein here may be carried out by an ordinal method known in this art. For example, KLH used as a carrier protein is maleimidated to bind the antigenic polypeptide. In this method, KLH is maleimidated by reacting with, preferably, a bifunctional condensing agent such as Sulfo-SMCC (sulfosuccimidyl 4-(N-maleimidomethyl)cyclohexane-1-carboxylate), followed by reaction with the antigenic polypeptide in which cysteine is added to one end desired for binding, the amino end or the carboxyl end of the peptide. As a result, the maleimidated KLH can readily bind to the antigenic polypeptide through thiol and thereby, an antigen for immunization is prepared. Alternatively, if carbodiimide is used, the KLH and the polypeptide can be bound together by forming a peptide bond with dehydration condensation between KLH and the antigenic polypeptide.

A solution containing the immunogen prepared as described above is mixed with an adjuvant, if necessary, and an animal generally used for producing an antibody (e.g. mouse, rat, rabbit, guinea pig, sheep, or goat) is subcutaneously or intraperitoneally immunized with the mixture repeatedly every 2 to 3 weeks. Blood is taken from the immunized animal and serum is separated therefrom to obtain antiserum. In the present invention, although the obtained antiserum may be used without purification, it may also be purified for use by the method as described below. Methods of purifying an antibody include: a method where serum is heat-treated to inactivate the complement, followed by salting-out using ammonium sulfate; a method of purifying an immunoglobulin fraction by, for example, ion exchange chromatography; and a method of purifying an antibody by affinity column chromatography using a column on which a certain polypeptide is immobilized. Of those, the method using affinity column chromatography is preferable. Here, as a polypeptide for purification that is immobilized on a column (hereinafter, which is also referred to as a "polypeptide for purification"), a polypeptide having the same sequence or the sequence of a portion thereof may be selected depending on the amino acid sequence of the antigenic polypeptide used for immunization.

Examples of a combination of the antigenic polypeptide with the polypeptide for purification include combinations of a polypeptide 118-131 with a polypeptide 121-128, of a polypeptide 118-131 with a polypeptide 118-131, of a polypeptide 121-128 with a polypeptide 121-129, and of a polypeptide 121-129 with a polypeptide 121-128. Of those, the combination of the polypeptide 118-131 with the polypeptide 121-128 is preferred. More particularly, using an antigenic polypeptide chemically synthesized, an immunogen is prepared by the above-mentioned method to immunize an animal such as a rabbit. Antiserum obtained from the animal according to the above method may be purified by an affinity column on which a polypeptide for purification is immobilized. By taking the case in which a combination of the polypeptide 118-131 as the antigenic polypeptide with the polypeptide 121-128 as the polypeptide for purification is used as the most preferable combination to prepare an antibody by affinity purification, the method of preparing the antibody of the present invention will be described in more detail.

At first, keyhole limpet hemocyanin (KLH) is reacted with Sulfo-SMCC (sulfosuccimidyl 4-(N-maleimidomethyl)cyclohexane-1-carboxylate) and dialysis is carried out in an appropriate buffer or the like to prepare maleimidated KLH. The polypeptide 118-131 to which cysteine is added at the amino end thereof is prepared by chemical synthesis and reacted with the maleimidated KLH, followed by dialysis against a physiological saline solution or the like to obtain an immunogen. A rabbit or the like is repeatedly immunized with this immunogen to obtain antiserum, which is subsequently loaded and absorbed onto an affinity column on which the polypeptide 121-128 is immobilized. The absorbed fraction can be eluted in an appropriate elution buffer or the like to obtain the antibody of the present invention that has been affinity purified.

Alternatively, if a monoclonal antibody is produced, an antibody-producing cell is collected from the spleen of an animal immunized by the same method as described above and fused with a cultured cell such as a myeloma cell by a standard method to generate a hybridoma (Koehler and Milstein, Nature, 256, 495-497 (1975)). From a culture medium of the hybridoma or the like, a monoclonal antibody that recognizes an epitope of interest may be selected.

Any of the antibodies obtained as described above is an antibody that recognizes the amino acid sequence of the above Exon 4-5 connective portion and specifically binds to a tau protein derived from a central nervous tissue but not a tau protein derived from a peripheral tissue regardless of the presence or absence of phosphorylation. This can be confirmed by using extracts from a central nervous tissue such as the brain and from a peripheral tissue such as the muscle to compare the reactivity of the antibody, or by analyzing the reactivity of the antibody with an insertion sequence inserted into the above Exon 4-5 connective portion, for example, a polypeptide having the amino acid sequence (SEQ ID NO: 2) encoded by Exon 4A of a gene encoding a tau protein, or by other methods.

3. Preparation of Sample for Carrying Out Detection of Alzheimer's Disease

In the present invention, a sample of interest for analysis includes body fluid such as blood, cerebrospinal fluid, or urine that is obtainable from an individual suspected of Alzheimer's disease, and blood is especially preferred. For example, in the case of blood, blood is taken from the vein of the elbow or the like of an individual suspected of Alzheimer's disease with a blood-collection tube or the like, and plasma or serum is separated therefrom by a preferred method such as centrifugation, and thereby a sample is obtained. In the case where cerebrospinal fluid is used as a sample, the fluid is taken from an individual suspected of Alzheimer's disease by, for example, lumbar puncture under anesthesia and a sample is obtained preferably by subjecting the fluid to centrifugation.

For the foregoing diseases other than Alzheimer's disease in which the deviation of a CNS tau protein from a central nervous tissue to body fluid may occur, a sample for use can be obtained from an individual suspected of each of the diseases in a similar manner. For example, body fluid such as blood, cerebrospinal fluid, or urine from an individual suspected of Down's syndrome, Parkinson's syndrome, Pick disease, progressive supranuclear palsy (PSP), corticobasal degeneration (CBD), or the like can be utilized.

Preferably, the obtained sample is supplemented with an enzyme inhibitor at the time of or after the collection of the sample in order to prevent the change of a tau protein (fragmentation, dephosphorylation, etc.,) or the coagulation of blood in the sample. Examples of enzyme inhibitors that can be utilized include: phosphatase inhibitors such as EDTA, EGTA, okadaic acid, pyrophosphoric acid, phosphate, sodium fluoride, β-glycerophosphoric acid, and cyclosporine A; and protease inhibitors such as aprotinin, antipain, pepstatin, leupeptin, EDTA, EGTA, PMSF (phenylmethanesulfonylfluoride), and TLCK (tosyl lysine chloromethyl ketone).

As the phosphatase inhibitor, each of EDTA and EGTA is preferred. In addition, the concentration of a phosphatase inhibitor added to a sample is not particularly limited as long as the concentration has an inhibitory effect on the activity of a phosphatase present in the sample. The combination of optimum concentrations of phosphatase inhibitors used may be determined, depending on the types of the phosphatase inhibitors. For example, EDTA and EGTA are usually used in the range of 1 to 1,000 mM, preferably in the range of 1 to 100 mM. As the protease inhibitor, aprotinin is preferred. Similarly, the concentration of a protease inhibitor added to a sample is not particularly limited as long as the concentration has an inhibitory effect on the activity of a protease present in the sample. For example, aprotinin is usually used in the range of 0.1 μM to 1,000 mM, preferably used in the range of 1 μM to 100 mM.

Of those, as a most preferable sample used in the present invention, plasma is employed that is obtainable by collecting blood using a blood-collection tube or the like supplemented with EDTA and aprotinin and centrifuging the blood. Alternatively, if cerebrospinal fluid is used as a sample, cerebrospinal fluid collected using a sample tube or the like supplemented with EDTA and aprotinin may be subjected to the analysis of a CNS tau protein, without being treated. It is preferred that those samples are stored, for example, at 4° C. or lower after collection until they are subjected to the analysis of a CNS tau protein, and it is more preferable that they are frozen and stored at −20° C. or lower.

Furthermore, if desired, such a sample is treated by denaturation in the presence of a protein-solubilizing agent to remove concomitant proteins (hereinafter, which is also referred to as "deproteinization") It is also preferable to use this treated sample as a sample. Especially, if blood is used as a sample, it is preferred to carry out deproteinization for the reason such as the hindrance of antigen-antibody reaction due to a high concentration of concomitant proteins. In the case of using a small amount of a blood sample, procedures for deproteinization can be omitted because hindrance by concomitant proteins is small. However, if there is a problem associated with the hindrance by concomitant proteins in a large amount of a blood sample to be used, procedures for deproteinization are preferably carried out. In addition, optionally, a sample that is further condensed can also be used as a sample in the method of the present invention.

A protein-solubilizing agent that can be used in the above treatment is not particularly limited as long as it has an effect of solubilizing a protein that is hardly soluble in water. Specific examples thereof include guanidine or a salt thereof, an agent containing a sulfhydryl group (hereinafter, which is also referred to as a "SH group-containing agent"), urea, and a surfactant. Each of those substances can be used alone or two or more of them can be used in combination. Of those, a combination of the guanidine salt and the SH group-containing agent is preferably used. Examples of a guanidine salt include a variety of guanidine salts with acids such as isothiocyanate, hydrochloride, and perchlorate. Of those, guanidine isothiocyanate and guanidine perchlorate are preferred. Examples of the SH group-containing agent include β-mercaptoethanol, dithiothreitol, and N-acethylcysteine, and β-mercaptoethanol is especially preferred. Examples of a preferred combination of the guanidine salt and the SH group-containing agent as a protein-solubilizing agent to be added in a blood sample include a combination of guanidine perchlorate and β-mercaptoethanol and a combination of guanidine isothiocyanate and β-mercaptoethanol.

Examples of the surfactant include Tween 20 (manufactured by ICI Americas Inc.), Triton X-100 (manufactured by Rohm & Haas), and Nonidet P40 (manufactured by Shell International Petroleum Company Ltd).

The concentration of a protein-solubilizing agent used in the present invention is usually 0.01 M, preferably 0.1 M, at a lower limit and 10 M, preferably 6 M, at an upper limit. The concentration range is selected from combinations of such a lower limit and an upper limit and the suitable range is usually 0.01 to 10 M, preferably approximately 0.1 to 6 M. Those concentration ranges are provided as a guideline and more particularly, optimum concentrations are preferably determined depending on the types of protein-solubilizing agents and a combination thereof. For example, the concentration of guanidine salt is in the range of usually 1 mM to 6 M, preferably 0.5 to 1 M. The concentration of a SH group-containing agent is usually in the range of 1 mM to 1 M, preferably in the range of 50 to 500 mM. The concentration of a surfactant is usually in the range of 0.001 to 0.5% (v/v), preferably in the range of 0.01 to 0.2% (v/v). Similarly, the concentration of urea is usually in the range of 2 to 10 M, preferably in the range of 5 to 7 M. It is noted that the numerical ranges of concentrations and the like used herein may be the ranges of the respective combinations of a lower limit and an upper limit illustrated similarly as above unless otherwise specified.

The above protein-solubilizing agent is added to a blood sample and the sample is diluted two-fold or greater, preferably 2 to 10 fold, followed by mixing with stirring to allow proteins in the sample to be solubilized. For diluting a sample, a solution such as TBS (150 mM/NaCl, 20 mM Tris-HCl (pH 7.5)) is used.

Next, concomitant proteins dissolved as described above in a sample solution are denatured and removed from the sample solution. Examples of a method for the denaturation treatment of concomitant proteins include: a method of treating concomitant proteins with a protein-denaturing agent such as trichloroacetic acid, trifluoroacetic acid, ammonium sulfate, urea, or an organic solvent; a method utilizing an interface; and a method by means of heating, which may be used alone or in combination. Each treatment condition may be a condition under which concomitant proteins contained in a sample solution are denatured but a tau protein therein is not denatured. Of those, preferably used in the present invention is the method by means of heating, and more preferably, boiling, that is, a method in which heating is carried out by boiling to 100° C. is used. Moreover, it is more preferred that boiling be carried out in the presence of NaCl at a concentration of 0.2 M or more. The boiling (heating) time is usually 1 to 15 minutes, preferably 3 to 10 minutes. As a method for boiling, a warm bath is preferred.

The concomitant proteins treated by solubilization and denaturation can be separated by an ordinal solid-liquid separation method known in this art, for example, a membrane separation method or a centrifugation method, and thereby deproteinization can be performed. Preferably, separation is carried out by centrifugation. In the case of denaturation treatment by boiling and heating, followed by centrifugation, a tau protein does not undergo denaturation by heating and is collected within a supernatant after centrifugation.

The sample obtained above can be further condensed if necessary according to a method known in this art to increase the sensitivity of detecting a tau protein. Examples of a condensation method include a method involving lowering salt concentrations by ultrafiltration, dialysis, gel filtration, or the like, followed by specific condensation by immunoprecipitation using magnetic beads or the like on which an anti-tau protein antibody is immobilized. Alternatively, the sample may be condensed by a solid-phase extraction method. In particular, the sample is added to, for example, a general solid phase for extraction where hydrocarbon with a low molecular weight is immobilized on a silica gel or the like, and a tau protein is retained in the solid phase, and then impurities such as a salt are removed by washing. Subsequently, an organic solvent or a mixed solvent of water with an organic solvent is poured to flow out the tau protein that can be then collected and condensed by removing the solvent. Alternatively, a process of removing immunoglobulin-G by column chromatography or the like can be optionally performed. A Protein G-Sepharose column or the like is preferably used for the column chromatography.

4. Method of Detecting CNS Tau Protein

The present invention also relates to a method of detecting tauopathy in which the presence of a CNS tau protein in a sample obtained from an individual suspected of tauopathy is analyzed by using the antibody of the present invention. Tauopathy is a disease that has neurodegeneration due to the accumulation of tau proteins in a central nervous tissue, and examples thereof include Alzheimer's disease, Down's syndrome, Parkinson's syndrome, Pick disease, progressive supra nuclear palsy (PSP), and corticobasal degeneration (CBD). More preferably, the detection method of the present invention is used for detecting Alzheimer's disease.

Hereinafter, by taking the detection of Alzheimer's disease as an example, the method of the present invention will be described. Namely, for a sample solution obtained from an individual suspected of Alzheimer's disease and applied to, if desired, treatments such as the solubilization of proteins and the denaturation of concomitant proteins, deproteinization, and condensation, the presence of a CNS tau protein is analyzed using the antibody specific to a CNS tau protein of the present invention. The analysis method of the presence of a CNS tau protein is not particularly limited as long as it is carried out by using the antibody specific to a CNS tau protein of the present invention. The analysis may be performed according to a method with which a reactivity of the antibody specific to a CNS tau protein to the sample, that is, an immune reaction between the protein contained in the sample and the antibody, can be compared with an immune reaction between a positive control and the antibody. By comparing the result from the use of the positive control having a known concentration with the result from the use of the sample, the amount of the CNS tau protein in the sample can be determined.

The analysis by the immune reaction between the antibody of the present invention and the protein in the sample obtained from an individual suspected of Alzheimer's disease can be carried out by an ordinal method known in this art, which is described in laboratory manuals such as Biochemical Experimental Method 11 "Enzyme Immunoassay" (by Tijssen P., Tokyo Kagaku Dojin), and "Antibodies: A LABORATORY MANUAL" (Ed Harlow et al., Cold Spring Harbor Laboratory (1988)). In particular, examples of the method include: immunoblotting; sandwich methods such as enzyme-linked immunosorbent assay (ELISA); and competitive methods.

If a CNS tau protein is analyzed by the sandwich method or the like, an antibody used in combination with the antibody specific to a CNS tau protein of the present invention is an antibody that recognizes an epitope different from one which the antibody of the present invention recognizes, and preferably, an antibody that recognizes a tau protein regardless of kind of isoforms (hereinafter, which is also referred to as a "non-specific anti-tau protein antibody") is used. Specific examples of the non-specific anti-tau protein antibody include anti-tau protein monoclonal antibodies HT7 (that binds to amino acid numbers 159-163 of a tau protein) and BT2 (that binds to amino acid numbers 193-198 of a tau protein) commercially available from Innogenetics.

Preferably, the non-specific anti-tau protein antibody is an antibody that recognizes a tau protein regardless of the presence of phosphorylation. When this antibody is used in combination with an antibody that recognizes a tau protein phosphorylated at the phosphorylation site specific to Alzheimer's disease, a change specific to Alzheimer's disease can be further detected. Examples of such an antibody include: an anti-phosphorylated tau protein antibody described in International Publication No. WO97/34145; and an anti-tau protein antibody prepared according to the description of the publication such as anti-PSI99, anti-PS202, anti-PT205, anti-PT231, anti-PS235, anti-PS262, anti-PS396, anti-PS404, anti-PS413, anti-PS422, or anti-tau 154-168.

If the advantage that the antibody of the present invention specifically recognizes a CNS tau protein but not a peripheral tau protein is exploited to analyze the presence of a CNS tau protein by immunoblotting or the like, more reliable analysis can be conducted by comparing with, for example, the result obtained by using an antibody that specifically recognizes a peripheral tau protein (hereinafter, which is also referred to as an "antibody specific to a peripheral tau protein"). Examples of the antibody specific to a peripheral tau protein include an antibody obtained by using, as an antigen, a polypeptide having all of or a portion of an amino acid sequence (SEQ ID NO: 2) encoded by Exon 4A of a gene encoding a tau protein.

Specific examples of the antibody include an antibody obtained by using an immunogen in which KLH is bound to a polypeptide where cysteine is introduced to the amino end of an amino acid sequence described in SEQ ID NO: 6 of the sequence listing (hereinafter, which is also referred to as an "anti-Exon 4A antibody"). A method of producing the antibody can utilize an ordinal method known in this art as above described method of producing the antibody specific to a CNS tau protein. The anti-Exon 4A antibody thus produced specifically binds to a peripheral tau protein having, as an insertion sequence, an amino acid sequence encoded by Exon 4A, regardless of the presence or absence of phosphorylation.

Here, by exemplifying the analysis of the presence of a CNS tau protein in a sample by ELISA, the method will be described.

At first, as an antibody for immobilization, either of the antibody specific to a CNS tau protein of the present invention or a non-specific anti-tau protein antibody is immobilized on a 96-well ELISA plate and a sample obtained by the method as described in the above 3 is added thereto to bind a tau protein in the sample to the solid phase. Next, as an antibody to detect the bound tau protein, the antibody other than the immobilized antibody is added, which is either the non-specific anti-tau protein antibody or the antibody specific to a CNS tau protein of the present invention, and the plate is incubated. Although a combination of antibodies used herein includes those described above, it is usually preferred that an antibody having higher specificity against the substance to be measured, that is, the antibody specific to a CNS tau protein in this case is immobilized and an antibody having lower specificity and broad reactivity, that is, the non-specific anti-tau protein antibody in this case is used for detection. However, by taking into consideration the degree of affinity of each antibody employed, and so on, they may be used in reverse.

Following incubation, the plate is washed in a washing solution andreactedwithanotherantibodythatrecognizestheantibodyfordetection and is labeled with a labeling substance, for example, an enzyme-labeled anti-rabbit IgG antibody. Alternatively, the antibody for detection that has been previously incorporated with biotin or the like is reacted with enzyme-labeled streptavidin. After wash in a washing solution, the activity of the labeling substance bound to the solid phase can be measured and compared with the result obtained by using a positive control having a known concentration to measure the amount of a CNS tau protein in the sample.

Next, another example of the analysis method will be described hereinafter, by exemplifying a method of detecting the presence of a CNS tau protein in a sample by immunoblotting.

To the sample obtained by the method as described in the above 3, an appropriate treatment solution, for example, a Laemmli sample buffer solution (0.125 M Tris-HCl (pH 6.8), 4% SDS, 20% glycerol, 20 µg/mL BPB, and 0.7 M β-mercaptoethanol) is added and the whole solution is heat-treated. This solution is subjected to electrophoresis with a polyacrylamide gel of 7 to 15% by the Laemmli's method (Nature, 227, 680-685 (1970)) and transferred to a membrane generally used for protein transfer such as a PVDF (polyvinyliden difluoride) membrane with an ordinal protein transfer apparatus such as a semi-dry blotter.

The resulting membrane is blocked in a protein solution such as skim milk and then reacted with the antibody specific to a CNS tau protein. After washing to remove the unreacted antibody, the membrane is reacted with a secondary antibody that has been previously incorporated with a labeling substance. If the labeling substance is, for example, such a substance as an enzyme which does not emit a signal by itself, the membrane after the reaction is washed and the unreacted secondary antibody is removed, followed by reacting with a substance such as a substrate that specifically reacts with the labeling substance, and the signal emitted from the reaction is detected. The detection result can be compared with the result obtained by using a positive control having a known concentration to determine the abundance of the tau protein in the sample. Examples of an enzyme used as a labeling substance include alkaline phosphatase, horseradish peroxidase (hereinafter, which is also referred to as "HRP"). Moreover, examples of a method of detecting a signal include a chemiluminescence method and a color development method. Of those, the chemiluminescence method is preferably used.

If the labeling substance is, for example, a substance such as a fluorescent substance or a radioactive substance which emits a signal by itself, the membrane after the reaction is washed and the unreacted secondary antibody is removed, followed by detecting a signal emitted by the labeling substance. The detection result can be compared with the result obtained by using a positive control having a known concentration to determine the abundance of the tau protein in the sample.

Additionally, in such a detection, in order to eliminate the effect caused by antibodies brought in from a sample or the like, the reaction of a substance having a specific binding ability instead of antigen-antibody reaction can be utilized. For example, a combination of biotin and streptavidin or a combination of digoxigenin and an anti-digoxigenin antibody is used as the substance having a specific binding ability, and among them, the combination of biotin and streptavidin is especially preferred.

A positive control used in the detection method of the present invention may be any substance that specifically binds to the antibody specific to a CNS tau protein of the present invention, and examples thereof include a tau protein lacking an insertion sequence between amino acid No. 124 and No. 125 of the sequence described in SEQ ID NO: 1 of the sequence listing. Alternatively, the positive control may be a fragment comprising an amino acid sequence of the connective portion (Exon 4-5 connective portion) between the amino acid sequence encoded by Exon 4 of a gene encoding a tau protein and the amino acid sequence encoded by Exon 5 thereof, or the like. Specific examples thereof include: a tau protein purified from a central nervous tissue of a human being, rabbit, or the like; a tau protein prepared by gene recombination and a fragment thereof; and a synthesized polypeptide.

A method of purifying a tau protein from a tissue can be an ordinal method known in this art. For example, a tau protein can be purified from a brain tissue according to a method such as that described in Journal of Neuroscience Research, 25, 412-419 (1990). Similarly, a genetically-engineered tau protein is prepared according to a method known in this art. However, any of those having the full-length of an amino acid sequence described in SEQ ID NO: 1 and those having a portion thereof can be also used as long as it specifically binds to the antibody of the present invention. Preferably used as the amino acid sequence of a portion thereof is, for example, a fragment containing an Exon 4-5 connective portion such as a fragment having 1-249 residues from the amino end of a tau protein (amino acid numbers 1-249 of SEQ ID NO: 1) or a fragment without an insertion sequence corresponding to amino acid numbers 45-102 of the above fragment (SEQ ID NO: 7; hereinafter, which is also referred to as a "shortest tau N-side fragment"). In addition, a standard protein supplied in a commercially available kit (Finoscolor hTAU or INNOTEST hTAU Ag; manufactured by Innogenetics) may also be used.

It is preferred that a tau protein or a peptide used as a positive control is, for example, stored as a freeze-dried powder or dissolved in an appropriate buffer for cryopreservation in small quantities. For example, 1 mg of the powder can be dissolved in 100 μL of TBST (20 mM Tris HCl buffer (pH 7.5) containing 150 mM NaCl and 0.05% Tween 20) and frozen and stored in a small quantity of 10 to 20 μL.

As mentioned above, for an individual suspected of Alzheimer's disease, the amount of a CNS tau protein in a sample obtained from the individual is measured and compared with the amount of the protein in a sample obtained from a normal subject. The individual having significantly large amount of a CNS tau protein can be diagnosed as having Alzheimer's disease. If there is no difference between the amount of the CNS tau protein measured in the sample obtained from the normal subject and the amount of the protein in the sample obtained from the individual subjected of Alzheimer's disease, this individual can be diagnosed as not having Alzheimer's disease. Preferably, such comparison is carried out using homogeneous samples obtained from each of individuals to be compared.

In the comparison of the amount of a CNS tau protein in a sample obtained from an individual suspected of Alzheimer's disease with the amount of the protein in a sample obtained from a normal subject, a mean value that has been previously obtained by carrying out measurement with plural samples may be used as the amount of the protein in the sample obtained from the normal subject. Such a mean value is desired to be a value that takes into consideration the ages of individuals from which samples are obtained. Here, "significantly large" means that the amount of a CNS tau protein contained in a sample obtained from an individual suspected of Alzheimer's disease is, for example, twice or more as high as the amount of the tau protein in a sample obtained from a normal subject, and then the individual is diagnosed as having Alzheimer's disease. Alternatively, standard deviation may be determined by statistical analysis to access whether there is significant difference or not.

Moreover, for example, if the respective average value of the amounts of CNS tau proteins contained in a sample obtained from an individual suspected of Alzheimer's disease and in a sample obtained from a normal subject have been obtained, a threshold value for assessment can be set. When the measured sample contains the CNS tau protein having the amount beyond this value, the individual can be diagnosed as having Alzheimer's disease. It is desired to set such a threshold value by taking into consideration the age of the individual from which the sample is obtained. Furthermore, if the amount of CNS tau proteins in samples obtained from normal subjects of cohort is at or below a detection limit, an individual can be diagnosed as having Alzheimer's disease when a CNS tau protein is detected in a sample obtained from the individual suspected of Alzheimer's disease.

Similarly, for a variety of diseases other than Alzheimer's disease as described above, the diagnosis can be carried out on the basis of the detected amount of a CNS tau protein.

5. Reagent Kit

A reagent kit of the present invention includes at least an antibody specific to a CNS tau protein and is provided with components according to a kit utilized for normal immune reaction. The reagent kit further includes, as optional components, a washing solution, a labeled antibody for detection, a pretreatment solution containing a protein-solubilizing agent, a positive control, a diluent, a protein-denaturing agent, and an apparatus or a reagent for condensation.

More particularly, in the case of a kit applied to ELISA, the kit includes at least the antibody specific to a CNS tau protein of the present invention, and additionally, an immobilized anti-tau protein antibody and a labeled anti-IgG antibody, and includes, as an optional component, a pretreatment solution containing a protein-solubilizing agent. Alternatively, in the case of a kit applied to a competitive method, the kit includes a labeled tau protein and an antibody specific to a CNS tau protein, and includes, as an optional component, a pretreatment solution containing a protein-solubilizing agent. In the case of a kit applied to a sandwich method using latex, the kit includes at least magnetic latex on which an antibody specific to a CNS tau protein or an anti-tau protein antibody is immobilized and a labeled antibody for detection, and includes, as an optional component, a protein-solubilizing agent. In the case of a kit applied to a competitive method using latex, the kit includes at least magnetic latex on which an antibody specific to a CNS tau protein is immobilized and a labeled tau protein, and includes, as an optional component, a pretreatment solution containing a protein-solubilizing agent.

The use of those reagent kits allows the method of detecting Alzheimer's disease of the present invention to be carried out more rapidly and conveniently.

EXAMPLES

Hereinafter, the present invention will be described by presenting examples, but the present invention is not limited to these examples.

In the examples as described below, "TBS" is 20 mM Tris-HCl buffer (pH 7.5) containing 150 mM NaCl and "TBST" is TBS containing 0.05% Tween 20.

For an antibody specific to a CNS tau protein prepared in the examples as described below, an antibody immunized by using a polypeptide 118-131 as an antigen and affinity-purified with a polypeptide 121-128 is indicated by an "anti-Exon 4-5 (118-131) antibody (121-128 purification)", an antibody immunized by using a polypeptide 118-131 as an antigen and affinity-purified with a polypeptide 118-131 is indicated by an "anti-Exon 4-5 (118-131) antibody (118-131 purification)", an antibody immunized by using a polypeptide 121-128 and affinity-purified with a polypeptide 121-129 as an antigen is indicated by an "anti-Exon 4-5 (121-128) antibody (121-129 purification)", and an antibody immunized by using a polypeptide 121-129 as an antigen and affinity-purified with a polypeptide 121-128 is indicated by an "anti-Exon 4-5 (121-129) antibody (121-128 purification)", unless otherwise specified. In addition, an anti-tau protein monoclonal antibody HT7 (that binds to the amino acid numbers 159-163 of a tau protein) is purchased for use from Innogenetics.

Example 1

Preparation and Evaluation of an Antibody

An antibody specific to a CNS tau protein was prepared according to the description of International Publication No. WO97/34145 as follows. Three polypeptides 118-131 (SEQ ID NO: 3), 121-128 (SEQ ID NO: 4), and 121-129 (SEQ ID NO: 5) were used as antigenic polypeptides. The resulting anti-sera were respectively purified using an affinity column on which a particular purified polypeptide for each of the anti-sera were immobilized, and the specificity of each of the antibodies were confirmed by dot blot analysis.

(1) Anti-Exon 4-5 (118-131) Antibody

A polypeptide 118-131 (SEQ ID NO: 3) to which cysteine was added at the amino end thereof was chemically synthesized as an antigenic polypeptide and bound to keyhole limpet hemocyanin (KLH), followed by the repeated immunization of a rabbit with the polypeptide to obtain antiserum. Specifically, 35 mg of KLH (a freeze-dried product; manufactured by Pierce) was dissolved in 7 mL of pure water and given as a buffer (83 mM phosphate buffer, 0.9 M NaCl (pH 7.2)). Subsequently, 43.75 mg of Sulfo-SMCC (sulfosuccimidyl 4-(N-maleimidomethyl) cyclohexane-1-carboxylate; manufactured by Pierce) was dissolved in 0.4 mL of DMSO (dimethylsulfoxide) and the solution was added to the buffer. The mixture was reacted at room temperature (25° C.) for 1 hour and was dialyzed overnight at 4° C. in an 83 mM phosphate buffer containing 100 mM EDTA and 0.9 M NaCl. The unreacted and degraded reagent was removed, and thereby maleimidated KLH was prepared. Next, to the dialyzed material (maleimidated KLH), 16.2 mg of the antigenic polypeptide (polypeptide where cysteine was added to the amino end of the polypeptide 118-131) was added and the whole was reacted at room temperature (25° C.) for 1 hour. After overnight dialysis against a physiological saline solution at 4° C., this dialyzed solution was adjusted to 17.5 mL with a physiological saline solution to be used as an antigen for immunization (immunogen).

A rabbit was repeatedly immunized with the resulting immunogen. Antiserum was collected and then loaded and absorbed onto columns on which two polypeptides for purification (a polypeptide 121-128 and a polypeptide 118-131 to which cysteine was added at the amino end thereof) were immobilized, respectively, and the absorbed fractions were eluted with a gentle elution buffer available from Pierce to obtain affinity-purified antibodies specific to a CNS tau protein (anti-Exon 4-5 (118-131) antibody (121-128 purification) and anti-Exon 4-5 (118-131) antibody (118-131 purification)). The confirmation of the specificity of the obtained antibodies was carried out by using enzyme-linked immunosorbent assay (ELISA) and dot blot analysis as described below to examine the binding to each antigenic polypeptide and a positive control.

In ELISA, to a 96-well plate on which an anti-tau protein monoclonal antibody HT7 (manufactured by Innogenetics) was immobilized, a recombinant shortest tau N-side fragment (SEQ ID NO: 7) prepared according to a method described in Brain Res., 737, 119-132 (1996) was added and incubated, followed by washing. Next, two antibodies obtained as described above were added and incubated, followed by washing. Then, an HRP-labeled anti-rabbit IgG antibody (goat) was added as a secondary antibody and the plate was washed. As a result of measuring the HRP activity of the solid phase, the enzyme activity (HRP activity) was increased in response to the concentration of the recombinant shortest N-side fragment, which confirmed that both of the two antibodies as obtained above binds to the recombinant shortest N-side fragment.

(2) Anti-Exon 4-5 (121-128) Antibody

A polypeptide 121-128 (SEQ ID NO: 4) was chemically synthesized and used for the preparation of an antibody. At first, 39 mg of porcine thyroid globulin (a freeze-dried product; manufactured by Sigma) was dissolved in 4 mL of pure water and the solution was supplemented with 1.4 mg of the synthesized polypeptide 121-128 and the pH was adjusted to 6.5 by adding an appropriate amount of 0.1 normal sodium hydroxide. To this solution, 76.7 mg of water-soluble carbodiimide hydrochloride was further added and the whole was reacted overnight at 4° C. After overnight dialysis at 4° C. against a physiological saline solution, the dialyzed solution was adjusted to 19.5 mL with a physiological saline solution to obtain an antigen for immunization (immunogen). A rabbit was repeatedly immunized with this immunogen to obtain antiserum. The antiserum was then loaded and absorbed onto a column on which a polypeptide where cysteine was added to the amino end of a polypeptide 121-129 (SEQ ID NO: 5) was immobilized. The absorbed fraction was eluted with a gentle elution buffer available from Pierce to obtain an affinity-purified antibody (anti-Exon 4-5 (121-128) antibody (121-129 purification)). The specificity of the obtained antibody was confirmed by dot blot analysis described below.

(3) Anti-Exon 4-5 (121-129) Antibody

A polypeptide where cysteine was added to the amino end of a polypeptide 121-129 (SEQ ID NO: 5) was chemically synthesized and 6.5 mg of this polypeptide was added to a solution prepared by dissolving 20 mg of maleimide activated KLH (a freeze-dried product; manufactured by Pierce) in 4 mL of pure water (83 mM phosphate buffer, 0.9 M NaCl, 0.1 M EDTA (pH 7.2)). The solution was reacted at room temperature (25° C.) for 1 hour and further reacted overnight at 4° C., followed by overnight dialysis at 4° C. against a physiological saline solution. The dialyzed solution was adjusted to 10 mL with a physiological saline solution to prepare an antigen for immunization (immunogen). Antiserum obtained by repeatedly immunizing a rabbit with this immunogen was loaded and absorbed onto a column on which a polypeptide 121-128 (SEQ ID NO: 4) was immobilized, and the absorbed fraction was eluted with a gentle elution buffer available from Pierce, and thereby an affinity-purified antibody (anti-Exon 4-5 (121-129) antibody (121-128 purification)) was obtained. The specificity of the obtained antibody was confirmed by dot blot analysis described below.

(4) Evaluation of Antibody by Dot Blot Analysis

The four antibodies prepared in the above (1)-(3) were evaluated for specificity by dot blot analysis.

At first, a DMSO solution (10 pmol/0.5 µL) of a recombinant shortest tau N-side fragment and a variety of polypeptides as antigens was dot-blotted on a PVDF membrane. Antigens employed are eight antigens: a recombinant shortest tau N-side fragment; a chemically synthesized polypeptide 24-36 (SEQ ID NO: 8); a polypeptide 118-131 (SEQ ID NO: 3) to which cysteine is added at the amino end thereof; a polypeptide 121-128 (SEQ ID NO: 4); a polypeptide 121-129 (SEQ ID NO: 5) to which cysteine is added at the amino end thereof; a polypeptide having a sequence of the portion of an amino acid sequence encoded by Exon 4A of a tau protein (SEQ ID NO: 6); a polypeptide 134-144 (SEQ ID NO: 9) to which tyrosine is added at the amino end thereof; and a polypeptide 154-156 (amino acid sequence Pro-Arg-Gly) to which cysteine is added at the amino end thereof.

After the membrane had been air-dried, it was blocked for 1 hour with 10 mL of TBS containing 5% skim milk, followed by washing five times in 20 mL of TBST. To the resulting membrane, the antibodies prepared in the above (1)-(3) which were dissolved in 5 mL of TBST containing 5% skim milk and adjusted to 500 ng/mL were added and the whole was reacted overnight at 4° C. in a humid box. Four antibodies were utilized: the anti-Exon 4-5 (118-131) antibody (121-128 purification); the anti-Exon 4-5 (118-131) antibody (118-131 purification); the anti-Exon 4-5 (121-128) antibody (121-129 purification); and the anti-Exon 4-5 (121-129) antibody (121-128 purification).

The membrane after the reaction was washed five times in 20 mL of TBST and reacted in a solution containing 0.25 mL of an alkaline phosphatase-labeled anti-rabbit IgG antibody solution (Simple Stain MAX-AP; manufactured by Nichirei) in 10 mL of TBST containing 5% skim milk at room temperature for 1 hour in a humid box. The membrane was washed five times in 20 mL of TBST to remove the unreacted labeled antibody. The membrane was further washed twice in 20 mL of TBS, and then placed in a humid box and immersed into 10 mL of a buffer (100 mM Tris-HCl (pH 9.5), 100 mM NaCl, 5 mM $MgCl_2$) containing an alkaline phosphatase substrate. To this reaction mixture, 66 µL of a NBT solution as a substrate (50 mg/mL nitro blue tetrazolium/70% dimethylfolmamide solution; manufactured by Promega) was added and mixed. Further, 33 µl of a BCIP solution (50 mg/mL 5-bromo-4-chloro-3-indolyl-phosphate/70% dimethylfolmamide solution; manufactured by Promega) was added thereto and mixed. Following the reaction at room temperature for 30 minutes, the membrane was washed three times in 20 mL of TBST to remove the unreacted substrate. As a result, the specificity of each of the antibodies was observed as shown in FIG. 1.

Here, as is evident from FIG. 1, the anti-Exon 4-5 (118-131) antibody (121-128 purification) reacted most strongly with the recombinant tau protein. The anti-Exon 4-5 (121-128) antibody (121-129 antibody purification) that had been expected to have higher specificity to the Exon 4-5 connective portion had low reactivity with the recombinant tau protein. On the other hand, the anti-Exon 4-5 (121-129) antibody (121-128 purification) showed higher reactivity with the recombinant tau protein than that with the antigenic polypeptide and was thus likely to be a potent antibody. In the studies as described below, it was decided to use the anti-Exon 4-5 (118-131) antibody (121-128 purification) that most highly reacted with the recombinant tau protein.

Example 2

Detection of CNS Tau Protein in Human Cerebrospinal Fluid by ELISA

Using the anti-Exon 4-5 (118-131) antibody (121-128 purification) selected in the above Example 1, analysis with cerebrospinal fluid as a sample was carried out by enzyme-linked immunosorbent assay (ELISA). In addition, using a tau-protein measuring kit (Finoscolor hTAU or INNOTEST hTAU Ag) commercially available from Innogenetics, measurement was carried out and compared with the method with the antibody of the present invention.

(1) Preparation of Human Cerebrospinal Fluid (CSF)

Cerebrospinal fluid as a sample was collected from each of an individual suspected of Alzheimer's disease (AD) and an individual having a neurological disease other than dementia (Control; CTL) by lumbar puncture under anesthesia after informed consent. The fluid was then centrifuged to obtain a supernatant for use.

(2) Immobilization of Anti-Human Tau Protein Antibody

To a 96-well ELISA plate, a 0.1 M sodium carbonate buffer (pH 9.0) containing an anti-human tau protein monoclonal antibody HT7 was added at 0.1 mL/well and incubated at 4° C. for 3 hours in a humid box to immobilize the antibody. After the solution was removed, the plate was washed in a 0.1 M sodium carbonate buffer and blocked at 4° C. for 2 hours by adding 0.2 mL of a PBS (10 mM sodium phosphate, 150 mM NaCl (pH 7.4)) solution containing 1% BSA, 1% skim milk, and 0.5% gelatin. The plate was used immediately after washing in a washing solution (20 mM Tris-HCl (pH 7.4), 0.05%

Tween 20). If not used immediately, the plate was further washed in pure water, dried under vacuum, and stored at 4° C. within a laminate bag.

(3) Measurement of CNS Tau Protein in Cerebrospinal Fluid by ELISA Using Antibody of the Present Invention According to a method described in International Publication No. WO97/34145, a CNS tau protein was measured as follows and compared with the concentration of a tau protein measured by using a commercially available tau protein measuring kit (trade name in Japan "Finoscolor hTAU" and trade name in the U.S. and Europe "INNOTEST hTAU Ag", manufactured by Innogenetics).

A genetically engineered shortest tau N-side fragment (SEQ ID NO: 7) obtained by introducing, into E. coli, a portion lacking an insertion sequence represented by amino acid numbers 45-102 in a gene encoding the amino acid numbers 1-249 of a tau protein, was measured using a commercially available tau protein measuring kit (trade name in Japan "Finoscolor hTAU" and trade name in the U.S. and Europe "INNOTEST hTAU Ag", manufactured by Innogenetics) to determine a value. This shortest tau N-side fragment used as a positive control was diluted at varying concentrations in an assay buffer (0.1% BSA, 1 mM EDTA, 1 mM EGTA, 20 mM Tris-HCl (pH 7.4), 0.15 M NaCl, 0.05% Tween 20) and each of the solutions containing each concentration was added at 50 µL/well to the ELISA plate prepared in the above (2). Similarly, each of the cerebrospinal fluids obtained in the above (1) was added at 50 µL/well to the ELISA plate. Subsequently, to each well containing the positive control having the fragment of known concentration or any of the human cerebrospinal fluids, 50 µL of the anti-Exon 4-5 (118-131) antibody (121-128 purification) prepared in the above Example 1 was added at the concentration of 100 ng/mL (an assay buffer containing 1% normal goat serum and 1% normal mouse serum), and then the plate was sealed with a plate sealer and incubated overnight at 4° C. with shaking.

After the plate was washed in a washing solution (20 mM Tris-HCl (pH 7.4), 0.15 M NaCl, 0.05% Tween 20), a peroxidase-labeled anti-rabbit IgG antibody solution (Simple Stain MAX-PO; manufactured by Nichirei) was diluted in an assay buffer containing 1% normal goat serum, 5% skim milk, and 1% normal mouse serum and added at 100 µL/well to the plate. The plate was sealed with a plate sealer and further incubated at 4° C. for 1 hour with shaking. After washing in the above washing solution again, a substrate solution was added at 0.1 mL/well to the plate and reacted with HRP immobilized on the solid phase at room temperature for 30 to 40 minutes to develop color. The substrate solution was prepared by dissolving 2.64 mg of TMB (3,3',5,5'-tetramethyl benzidine) in 0.1 mL of DMSO, adding the DMSO solution to 10 mL of a 0.1 M citric acid buffer (pH 4.4), and subsequently supplementing with 3.3 µL of a 30% hydrogen peroxide solution. For terminating reaction, 0.1 mL of 1 normal sulfuric acid was added, and the concentration of the CNS tau protein was determined by measuring absorbance at 450 nm with a plate reader.

(4) Measurement of Tau Protein in Cerebrospinal Fluid Using Commercially Available Kit Next, measurement was carried out using a commercially available tau protein measuring kit (trade name in Japan "Finoscolor hTAU" and trade name in the U.S. and Europe "INNOTEST hTAU Ag", manufactured by Innogenetics). According to all procedures in the instructions provided with the kit, 25 µL of each of the same samples as those used in the above (3) was used to measure the concentration of the tau protein.

(5) Analysis of Measurement

The results from the above (3) and (4) were analyzed and shown in Table 1.

TABLE 1

Concentrations (fmol/ml; pM) of CNS tau proteins (a) and tau proteins (b) in cerebrospinal fluids (CSF) from Alzheimer's disease patient (AD) and non-demented subject (CTL)

| Patient No. | CNS tau protein (a) | tau protein (b) | a/b |
|---|---|---|---|
| AD1 | 32.74 | 5.1 | 6.42 |
| AD2 | 48.94 | 10.0 | 4.89 |
| AD3 | 74.64 | 11.4 | 6.55 |
| AD4 | 52.07 | 11.1 | 4.69 |
| CTL1 | 10.41 | N. D. (<0.5) | — |
| CTL2 | 13.67 | N. D. (<0.5) | — |

As is evident from Table 1, the anti-Exon 4-5 (118-131) antibody (121-128 purification) was able to distinguish between the sample obtained from an individual suspected of Alzheimer's disease (AD) and the sample obtained from an individual with a neurological disease other than dementia (Control; CTL). Although the measurement result corresponded with that obtained by using the commercially available kit, its sensitivity of detecting a CNS tau protein was found to be much higher than that of the kit. Therefore, it has been demonstrated that the antibody of the present invention is very useful for the detection of Alzheimer's disease.

Example 3

Detection of CNS Tau Protein in Human Brain and Muscle Tissue by ELISA (1) Preparation of Sample For the sample of a brain tissue, a tau protein was extracted and purified from a brain tissue obtained at the time of the autopsy of an Alzheimer's disease patient (provided by Dr. Hiroyuki Shimada at the Tokyo Metropolitan Geriatric Medical Center in 1990) according to a method described in International Publication No. WO97/341345 (a method in accordance with a method described in H. Ksiezak-Reding et al., Journal of Neuroscience Research, 25, 412-419, 420-430 (1990)). A commercially available human muscle tissue extract (Cat No. #7804-1, from CLONTECH Laboratories, Inc.) was used as the sample of a muscle tissue.

Those samples were used to carry out measurement by enzyme-linked immunosorbent assay (ELISA) in the same manner as in the above Example 2.

(2) Immobilization of Anti-Human Tau Protein Antibody

An anti-human tau protein monoclonal antibody HT7 was immobilized on a 96-well ELISA plate in the same manner as in Example 2(2).

(3) Measurement of CNS Tau Protein in Brain and Muscle Tissue by ELISA Using Antibody of the Present Invention As in Example 2(3), a CNS tau protein was measured as follows and compared with the result measured by using a tau protein measuring kit manufactured by Innogenetics.

The genetically engineered shortest tau N-side fragment (SEQ ID NO: 7) whose value had been determined in the above Example 2 (3) was used as a positive control. The shortest tau N-side fragment with the determined concentration was diluted at varying concentrations in an assay buffer (0.1% BSA, 1 mM EDTA, 1 mM EGTA, 20 mM Tris-HCl (pH7.4), 0.15 M NaCl, 0.05% Tween 20) to prepare dilution series, each of which was then added at 50 μL/well to the ELISA plate prepared in the above (2). The brain and muscle tissue extracts prepared in the above (1) were respectively diluted in an assay buffer to prepare dilution series, each of which was subsequently added at 50 μL/well to the well of the ELISA plate in the same way.

To each well containing, as a sample, either the positive control having a known concentration of the fragment or the tissue extract, 50 μL of the anti-Exon 4-5 (118-131) antibody (121-128 purification) (100 ng/mL; in an assay buffer containing 1% normal goat serum and 1% normal mouse serum) was added, and the plate was sealed with a plate sealer and incubated overnight at 4° C. with shaking. After the reaction, the plate was washed in a washing solution (20 mM Tris-HCl (pH 7.4), 0.15 M NaCl, 0.05% Tween 20) and a peroxidase-labeled anti-rabbit IgG antibody (Simple Stain MAX-PO; manufactured by Nichirei) that was diluted in the above assay buffer was added at 100 μL/well to the plate. The plate was sealed with a plate sealer and incubated at 4° C. for 1 hour with shaking.

After wash in a washing solution, a substrate solution was added at 0.1 mL/well to the plate and reacted with HRP immobilized on the solid phase at room temperature for 30 to 40 minutes to develop color. The substrate solution was prepared by dissolving 64 mg of TMB (3,3',5,5'-tetramethyl benzidine) in 0.1 mL of DMSO (dimethyl sulfoxide), adding the DMSO solution to 10 mL of a 0.1 M citric acid buffer (pH 4.4), and subsequently supplementing with 3.3 μL of a 30% hydrogen peroxide solution. For terminating reaction, 0.1 mL of 1 normal sulfuric acid was added thereto, and the concentration of the CNS tau protein was determined by measuring absorbance at 450 nm with a plate reader.

(4) Measurement of Tau Protein in Brain and Muscle Tissues Using Commercially Available Kit For the samples prepared in the above (1), the concentration of the tau protein was measured using a commercially available tau protein measuring kit (trade name in Japan "Finoscolor hTAU" and trade name in the U.S. and Europe "INNOTEST hTAU Ag", manufactured by Innogenetics) According to the instructions provided with the kit, measurement was performed using 25 μL of each of the samples.

(5) Analysis of Measurement

The results from the above (3) and (4) were analyzed and shown in Table 2.

TABLE 2

Concentrations (pmol/ml; nM) of CNS tau proteins (a) and tau proteins (b) in brain extract from Alzheimer's disease patient (AD) and muscle extract from normal subject (CTL)

|  | CNS tau protein (a) | tau protein (b) | a/b |
|---|---|---|---|
| AD brain extract | 412 | 35 | 11.8 |
| CTL muscle extract | 1.8 | 1.0 | 1.8 |
| Brain/muscle | 229 | 35 | — |

As is evident from Table 2, the measurement method using the anti-Exon 4-5 (118-131) antibody (121-128 purification) of the present invention had reactivity with the tau protein as much as that of the commercially available kit, while the method exhibited extremely strong reaction with the CNS tau protein. The reactivity with the CNS tau protein was ten times or more as high as that of the commercial kit. As a result, it has been demonstrated that the antibody of the present invention does not react with a peripheral tau protein contained in a peripheral tissue such as the muscle or blood and can detect a CNS tau protein specifically and sensitively without hindrance of the peripheral tau protein.

Example 4

Detection of CNS Tau Protein in Human Brain and Muscle Tissues by Immunoblotting (1) Preparation of an Antibody An anti-tau protein monoclonal antibody HT7 was purchased from Innogenetics for use. The anti-Exon 4-5 (118-131) antibody (121-128 purification) prepared in the above Example 1 was used.

For an antibody specifically recognizing a peripheral tau protein (an antibody specific to a peripheral tau protein), an antibody obtained by immunization with an antigen, a polypeptide having a portion of an amino acid sequence encoded by Exon 4A of a gene encoding a tau protein was prepared as follows according to the description of International Publication No. WO97/34145.

A polypeptide having a sequence where cysteine was introduced into the amino end of the sequence of the portion of an amino acid sequence (SEQ ID NO: 6) encoded by Exon 4A of a gene encoding a tau protein was chemically synthesized as an antigenic polypeptide, and bound to keyhole limpet hemocyanin (KLH) to prepare an immunogen. At first, 1.5 mg of maleimidated KLH (a freeze-dried product; manufactured by Pierce) was dissolved in 0.15 mL of pure water (50 mM phosphate buffer, 0.15 M NaCl, 100 mM EDTA (pH 7.2)), and 3.0 mg of the above polypeptide was added to the solution, and reacted at room temperature (25° C.) for 2 hours. This solution was dialyzed overnight at 4° C. against a physiological saline solution and then adjusted to 1.0 mL with a physiological saline solution to prepare an antigen for immunization (immunogen). Antiserum was obtained from a rabbit repeatedly immunized with the resulting immunogen and the antiserum was loaded and absorbed onto a column on which the above polypeptide was immobilized, and the absorbed fraction was eluted with a gentle elution buffer available from Pierce, and thereby an affinity-purified antibody (hereinafter, which is also referred to as an "anti-Exon 4A antibody") was obtained.

For the specificity of this anti-Exon 4A antibody, the reactivity with a variety of synthesized polypeptides was analyzed by dot blot in the same manner as in the evaluation of the anti-Exon 4-5 antibody carried out in the above Example 1(4) and it was confirmed that the anti-Exon 4A antibody specifically reacted with the above antigenic polypeptide.

(2) Preparation of Sample

The brain tissue extract derived from an Alzheimer's disease patient and the commercially available human muscle tissue extract same as those in the above Example 3 (1) were used as samples. A genetically engineered tau protein (SEQ ID NO: 1) provided by Dr. Goedert (MRC Laboratory of Molecular Biology, UK) was used as a positive control.

(3) Analysis by Immunoblotting

Each of the tissue extracts and the positive control prepared in the above (2) was applied to a 9% polyacrylamide gel, subjected to electrophoresis by the Laemmli's method (Nature, 227, 680-685 (1970)), and transferred to a PVDF membrane with a semidry blotter. Three of such PVDF membranes were prepared and analyzed with immunoblotting using the anti-Exon 4-5 (118-131) antibody (121-128 purification), the anti-Exon 4A antibody (rabbit), and the anti-tau protein monoclonal antibody HT7 as follows.

The obtained PVDF membranes were blocked for 1 hour using 20 mL of TBS containing 5% skim milk as a blocking solution. Thereafter, this blocking solution was supplemented with the anti-Exon 4-5 (118-131) antibody (121-128 purification) at the concentration of 540 ng/mL, with the anti-Exon 4A antibody at the concentration of 1,300 ng/mL, or with the anti-tau protein monoclonal antibody HT7 at the concentration of 2,000 ng/mL, respectively. 15 mL of each of them was added to a membrane, followed by overnight reaction at 4° C. in a humid box. After the reaction, the membranes were washed three times in 20 mL of TBST for 10 minutes to remove the unreacted antibodies.

As an alkaline phosphatase-labeled secondary antibody, 0.75 mL of an anti-rabbit IgG antibody solution (Simple Stain MAX-AP manufactured by Nichirei) for the anti-Exon 4-5 (118-131) antibody (121-128 purification) and the anti-Exon 4A antibody, and 3 μL of an anti-mouse IgG antibody solution (manufactured by Promega) for the anti-tau protein monoclonal antibody HT7 were added to 15 mL of TBS containing 5% skim milk and reacted at room temperature for 1 hour in a humid box. After the reaction, the membranes were washed three times in 20 mL of TBST for 10 minutes to remove the unreacted secondary antibodies.

The membranes were placed in a humid box again and immersed in 15 mL of a buffer for an alkaline phosphatase substrate (100 mM Tris-HCl (pH 9.5), 100 mM NaCl, 5 mM $MgCl_2$). As a substrate, 100 μL of NBT solution (50 mg/mL nitro blue tetrazolium/70% dimethylfolmamide solution; manufactured by Promega) was added and BCIP solution (50 mg/mL 5-bromo-4-chloro-3-indolyl-phosphate/70% dimethylfolmamide solution; manufactured by Promega) was further added thereto, followed by mixing. Following the reaction at room temperature for 30 minutes, the membranes were washed three times in 20 mL of TBST for 10 minutes to remove the unreacted substrate.

Figure 2:
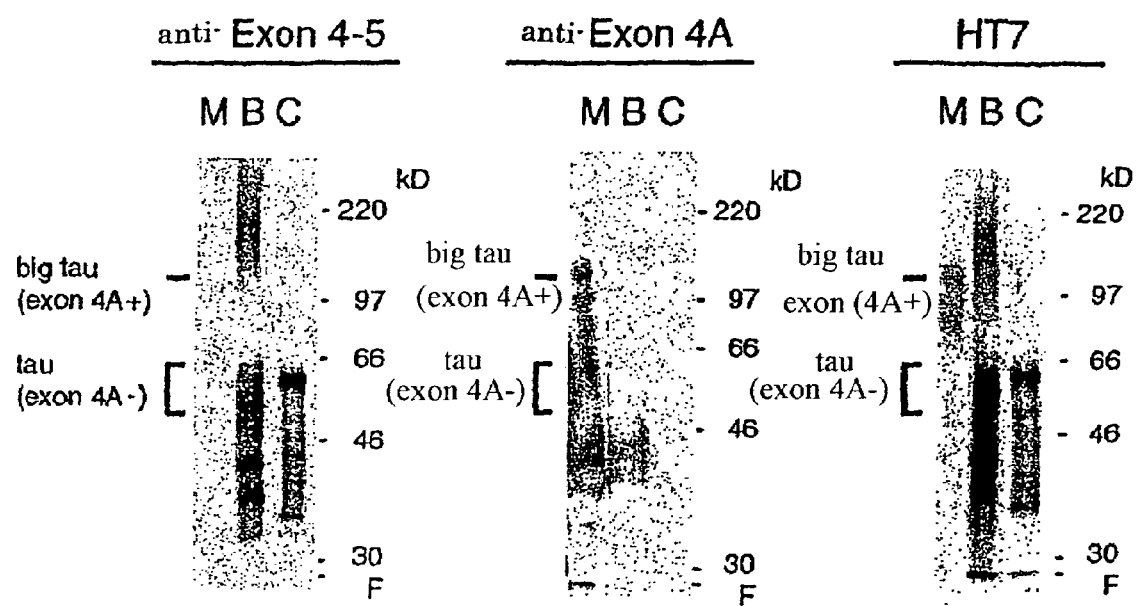
FIG. 2 shows a photographic diagram of western blot analysis of the specificity of the antibody of the present invention against a CNS tau protein. In this figure, "anti-Exon 4-5" is an anti-Exon 4-5 (118-131) antibody (121-128 purification), "anti-Exon 4A" is an anti-Exon 4A antibody, and "HT7" is an anti-tau protein monoclonal antibody HT7. "M" of a sample represents an extract of a human muscle tissue, "B" represents an extract of a brain tissue of an Alzheimer's disease patient, and "C" represents a positive control. "big tau" (exon 4A+) and "tau" (Exon 4A−) represent the band position of a peripheral tau protein and the band position of a CNS tau protein, respectively.

The result is shown in FIG. 2. In FIG. 2, lane M shows the image of the electrophoresis of the human muscle tissue extract, lane B shows that of the brain tissue extract from an AD patient, and lane C shows that of the genetically engineered tau protein (CNS tau protein) as a positive control.

The result of immunoblotting has revealed that there exist a peripheral tau protein with a molecular weight of 110 kD having, as an insertion sequence, an amino acid sequence encoded by Exon 4A (in the figure, which is indicated by "big tau (exon 4A+)") and fragments thereof in the human muscle tissue extract, and that they were detected by the anti-Exon 4A antibody and the anti-tau protein monoclonal antibody HT7, although they are almost absent in the brain tissue extract. On the other hand, it has been confirmed that the anti-Exon 4-5 (118-131) antibody (121-128 purification) does not react with the human muscle extract in any way and specifically reacts with only CNS tau proteins with a molecular weight of 48 to 65 kD (in the figure, which is indicated by "tau (Exon 4A−)"), and a polymerized material and fragments thereof, contained in the human brain tissue extract and the positive control.

As is obvious from those results, the antibody of the present invention can clearly distinguish CNS tau proteins derived from a central nervous tissue such as the brain from a peripheral tau protein derived from a peripheral tissue such as the muscle. Thus, it was suggested that even by using a sample derived from a peripheral tissue such as the blood or muscle that has been conventionally incapable of obtaining high sensitivity owing to the hindrance of a peripheral tau protein with a large molecular weight, CNS tau proteins can be detected specifically and sensitively.

Example 5

Detection of CNS Tau Protein in Human Blood by ELISA

It has been indicated in the above Example 4 that the antibody of the present invention can clearly distinguish a CNS tau protein derived from a central nervous tissue such as the brain from a peripheral tau protein derived from a peripheral tissue such as the muscle. Therefore, the antibody was used to detect a CNS tau protein in human blood containing a large amount of peripheral tau proteins.

(1) Preparation of Sample

Blood was collected from each of an individual suspected of Alzheimer's disease (AD) and a healthy volunteer individual (Control) through the vein of the elbow after informed consent and stored at −40° C. after the separation of plasma. The blood obtained from the individual suspected of Alzheimer's disease was purchased from Scripps Laboratories Japan, Inc.

(2) Immobilization of Anti-Human Tau Protein Antibody

To a 96-well ELISA plate (for the measurement of fluorescence/luminescence), a 0.1 M sodium carbonate buffer (pH 9.0) containing an anti-human tau protein monoclonal antibody HT7 was added at 0.1 mL/well and incubated at 4° C. for 3 hours in a humid box to immobilize the antibody. After the solution was removed, the plate was washed in a 0.1 M sodium carbonate buffer and blocked at 4° C. for 2 hours by adding 0.2 mL of a PBS solution (10 mM sodium phosphate, 150 mM NaCl (pH 7.4)) containing 1% BSA and 1% skim milk. The plate was used immediately after washing in a washing solution (20 mM Tris-HCl (pH 7.4), 0.05% Tween 20). If not used immediately, the plate was further washed in pure water, dried under vacuum, and stored at 4° C. within a laminate bag.

(3) Measurement of CNS Tau Protein in Blood by ELISA Using Antibody of the Present Invention According to a method described in International Publication No. WO97/34145, a CNS tau protein in the human blood was measured as follows.

At first, to the ELISA plate prepared in the above (2), an anti-Exon 4-5 (118-131) antibody (121-128 purification) (100 ng/mL; in an assay buffer (0.1% BSA, 1 mM EDTA, 1 mM EGTA, 20 mM Tris-HCl (pH 7.4), 0.15 M NaCl, 0.05% Tween 20) containing 5% skim milk, 1% normal goat serum, and 1% normal mouse serum) was added at 75 μL/well. To those respective wells, the blood sample prepared in the above (1) was added at 25 μL/well. Alternatively, the genetically engineered shortest tau N-side fragment (SEQ ID NO: 7) as a positive control that was measured in the above Example 2(3) with the commercially available tau protein measuring kit (trade name in Japan "Finoscolor hTAU" and trade name in the U.S. and Europe "INNOTEST hTAU Ag", manufactured by Innogenetics) was diluted at varying concentrations in an assay buffer to prepare dilution series and added at 25 μL/well to different wells. The plate was sealed with a plate sealer and incubated overnight at 4° C. with shaking.

After the reaction, the plate was washed in a washing solution (20 mM Tris-HCl (pH 7.4), 0.15 M NaCl, 0.05% Tween 20), and to the plate we added 100 μl/well of an alkaline phosphatase-labeled anti-rabbit IgG antibody (Simple Stain MAX-AP; manufactured by Nichirei) that was diluted in the above assay buffer (0.1% BSA, 1 mM EDTA, 1 mM EGTA, 20 mM Tris-HCl (pH7.4), 0.15 M NaCl, 0.05% Tween 20) containing 5% skim milk, 1% normal goat serum, and 1% serum mouse serum. The plate was sealed again with a plate sealer and incubated at 4° C. for 1 hour with shaking.

After wash in a washing solution, a luminescent substrate solution "CDP-star™" (Disodium 2-chloro-5-(4-metoxyspiro {1,2-dioxetane-3,2'-(5'-chloro)-tricyclo [$3.3.1.1^{3,7}$] decan}-4-yl)-1-phenyl phosphate) available from Applied Biosystems was added at 0.1 mL/well to the plate and reacted with alkaline phosphatase immobilized on the solid phase at room temperature for 40 to 50 minutes to emit light. Emission intensity was measured with a luminescence plate reader (LUMINUS CT9000: manufactured by DIA-IATRON) to determine the concentration of the CNS tau protein.

(4) Analysis of Measurement

The result obtained from the above (3) was analyzed and shown in Table 3.

TABLE 3

Concentrations (fmol/ml; pM) of CNS tau proteins in blood from Alzheimer's disease patient (AD) and normal subject (CTL)

| Sample No. | concentration of CNS tau protein |
|---|---|
| AD1 | 1.30 |
| AD2 | 1.91 |
| AD3 | 5.88 |
| AD4 | 1.43 |
| CTL1 | 0.41 |
| CTL2 | 1.05 |
| CTL3 | 0.81 |
| CTL4 | 0.48 |

As is evident from Table 3, it has been demonstrated that, if the antibody specific to a CNS tau protein of the present invention is used, the presence of a CNS tau protein can be analyzed even by using human blood with which detection of the CNS tau protein had been difficult owing to the large abundance of peripheral tau proteins, and the detection of Alzheimer's disease can be carried out.

Example 6

Detection of CNS Tau Protein in Human Blood by ELISA

It has been demonstrated in the above Example 5 that the antibody of the present invention is useful for analyzing the presence of a CNS tau protein even in human blood and thus the detection of Alzheimer's disease can be carried out. Thus, the antibody was further used for analysis using blood as a sample for a group of patients diagnosed as having Alzheimer's disease or MCI by a conventional method.

Of patients diagnosed as having MCI by the conventional method, 10 to 15% in a year and approximately 50% in several years are said to proceed to Alzheimer's disease and there is a growing acknowledgement that patients with early Alzheimer's disease are included in MCI patients. By evaluating such a group of patients with the present method, the possibility of detecting early Alzheimer's disease which had been hardly diagnosed by the conventional method was examined.

(1) Preparation of Sample (1) Preparation of sample

Blood was collected from each of an individual suspected of Alzheimer's disease (AD), an individual suspected of MCI, and a healthy volunteer individual (Control) after informed consent. Blood was taken through the vein of the elbow and stored at −40° C. after the separation of plasma.

The diagnosis of Alzheimer's disease was conducted on the basis of "Diagnostic and Statistical Manual of Mental Disorders, 4th ed., revised text (DSM-IV-TR)" (published by American Psychiatric Association, 2000) and the diagnosis of MCI was conducted on the basis of the criteria of Petersen, R. C. et al. (Arch. Neurol., 56, 303-308 (1999)).

(2) Immobilization of Anti-Human Tau Protein Antibody

To a 96-well ELISA plate (for the measurement of fluorescence/luminescence), a 0.1 M sodium carbonate buffer (pH 9.0) containing an anti-human tau protein monoclonal antibody HT7 was added at 0.1 mL/well and incubated at 4° C. for 3 hours in a humid box to immobilize the antibody. After the solution was removed, the plate was washed in a 0.1 M sodium carbonate buffer and blocked at 4° C. for 2 hours by adding 0.2 mL of a PBS solution (10 mM sodium phosphate, 150 mM NaCl (pH 7.4)) containing 1% BSA and 1% skim milk thereto. The plate was used immediately after washing in a washing solution (20 mM Tris-HCl (pH 7.4), 0.05% Tween 20). If not used immediately, the plate was further washed in pure water, dried under vacuum, and stored at 4° C. within a laminate bag.

(3) Measurement of CNS Tau Protein in Blood by ELISA Using Antibody of the Present Invention According to a method described in International Publication No. WO97/34145, a CNS tau protein in the human blood was measured as follows.

At first, to the ELISA plate prepared in the above (2), an anti-Exon 4-5 (118-131) antibody (121-128 purification) (50 ng/mL; in an assay buffer (0.1% BSA, 1 mM EDTA, 1 mM EGTA, 20 mM Tris-HCl (pH 7.4), 0.15 M NaCl, 0.05% Tween 20) containing 1% normal goat serum and 1% normal mouse serum) was added at 80 μL/well. To those respective wells, the blood sample prepared in the above (1) was added at 20 μL/well. Alternatively, the genetically engineered shortest tau N-side fragment (SEQ ID NO: 7) as a positive control that was measured in the above Example 2(3) with the commercially available tau protein measuring kit (trade name in Japan "Finoscolor hTAU" and trade name in the U.S. and Europe "INNOTEST hTAU Ag", manufactured by Innogenetics) was diluted at varying concentrations in an assay buffer to prepare dilution series and added at 20 μL/well to different wells. The plate was sealed with a plate sealer and incubated overnight at 4° C. with shaking.

After the reaction, the plate was washed in a washing solution (20 mM Tris-HCl (pH 7.4), 0.15 M NaCl, 0.05% Tween 20), and to the plate we added 100 μl/well of an alkaline phosphatase-labeled anti-rabbit IgG antibody (Simple Stain MAX-AP; manufactured by Nichirei) that was diluted in the above buffer (0.1% BSA, 20 mM Tris-HCl (pH7.4), 0.15 M NaCl, 0.05% Tween 20) containing 5% skim milk, 1% normal goat serum, and 1% serum mouse serum. The plate was sealed again with a plate sealer and incubated at 4° C. for 1 hour with shaking.

After wash in a washing solution, a luminescent substrate solution "CDP-star™" (Disodium 2-chloro-5-(4-metoxyspiro {1,2-dioxetane-3,2'-(5'-chloro)-tricyclo [$3.3.1.1^{3,7}$] decan}-4-yl)-1-phenyl phosphate) available from Applied Biosystems was added at 0.1 mL/well to the plate and reacted with alkaline phosphatase immobilized on the solid phase at 30° C. for 30 to 50 minutes to emit light. Emission intensity was measured with a luminescence plate reader (LUMINUS CT9000: manufactured by DIA-IATRON) and thereby, the concentration of the CNS tau protein was determined.

(4) Analysis of Measurement

The result obtained from the above (3) was analyzed and shown in Table 4.

TABLE 4

Concentrations (fmol/ml; pM) of CNS tau proteins in blood from Alzheimer's disease patient (AD), mild cognitive impairment (MCI), and normal subject (CTL)

| Sample No. | concentration of CNS tau protein |
|---|---|
| AD1 | 0 |
| AD2 | 0.39 |
| AD3 | 33.94 |
| AD4 | 3.11 |
| AD5 | 0.17 |
| AD6 | 3.17 |
| AD7 | 7.8 |
| AD8 | 0.18 |
| AD9 | 0 |
| AD10 | 0.58 |
| AD11 | 0.29 |
| AD12 | 0.08 |
| MCI1 | 6.82 |
| MCI2 | 25.84 |
| MCI3 | 4.06 |
| MCI4 | 0 |
| MCI5 | 0 |
| MCI6 | 0.36 |
| MCI7 | 4.58 |
| MCI8 | 0.37 |
| MCI9 | 0.16 |
| MCI10 | 6.7 |
| MCI11 | 8.57 |
| MCI12 | 4.66 |
| MCI13 | 9.12 |
| MCI14 | 3.19 |
| MCI15 | 3.2 |
| MCI16 | 12.02 |
| CTL1 | 0.5 |
| CTL2 | 0.26 |

TABLE 4-continued

Concentrations (fmol/ml; pM) of CNS tau proteins in blood from Alzheimer's disease patient (AD), mild cognitive impairment (MCI), and normal subject (CTL)

| Sample No. | concentration of CNS tau protein |
|---|---|
| CTL3 | 0 |
| CTL4 | 0.12 |
| CTL5 | 0.29 |
| CTL6 | 0.33 |
| CTL7 | 0 |
| CTL8 | 0.14 |
| CTL9 | 0.51 |
| CTL10 | 0.91 |

As is evident from Table 4, it has been demonstrated that if the antibody specific to a CNS tau protein of the present invention is used, the presence of a CNS tau protein can also be analyzed by using human blood as a sample for a group of patients diagnosed as having MCI by a conventional method. Moreover, it has been confirmed that a small amount of a sample could be used to carry out analysis without pretreatment and that the use of a chemiluminescence method could attain much higher sensitivity. That is, the antibody and the detection method of the present invention were confirmed to have high sensitivity.

INDUSTRIAL APPLICABILITY

The use of the antibody of the present invention allows the specific analysis of a CNS tau protein even by using a sample derived from a peripheral tissue such as blood. Consequently, the more convenient and sensitive detection of Alzheimer's disease can be performed without collecting cerebrospinal fluid or the like that causes large invasiveness to patients, and thus the antibody of the present invention can be used as a means that assists in the decision on therapeutic courses, the assessment of therapeutic effects, the decision on aged care standards, and so on.

The invention claimed is:

1. An isolated antibody specific to a central nervous system (CNS) tau protein, wherein the antibody specifically recognizes a CNS tau protein but not a peripheral tau protein, wherein the antibody is obtained by immunizing an animal with a polypeptide comprising an amino acid sequence specific to the CNS tau protein consisting of amino acid residues 124-125 of SEQ ID NO: 1 and wherein the antibody specifically recognizes the amino acid sequence specific to CNS tau protein as contained in a polypeptide consisting of amino acid residues selected from the group consisting of 121-128 of SEQ ID NO: 1, 118-131 of SEQ ID NO: 1, and 121-129 of SEQ ID NO: 1.

2. The antibody according to claim 1, wherein the antibody is obtained by immunizing the animal with a polypeptide which has a length of 5 to 20 amino acid residues and comprises the amino acid sequence specific to the CNS tau protein.

3. A reagent kit for detecting Alzheimer's disease comprising at least the antibody as claimed in claim 1.

4. A method of producing an antibody specific to a CNS tau protein comprising:
immunizing an animal with a polypeptide containing an amino acid sequence specific to a CNS tau protein as an antigen, wherein the amino acid sequence specific to a CNS tau protein consists of amino acid residues 124-125 of SEQ ID NO: 1;
analyzing reactivity of a resulting antibody with the CNS tau protein and a peripheral tau protein; and
selecting an antibody having reactivity specific to the CNS tau protein, wherein the antibody specifically recognizes the amino acid sequence specific to CNS tau protein as contained in a polypeptide consisting of amino acid residues selected from the group consisting of 121-128 of SEQ ID NO: 1, 118-131 of SEQ ID NO: 1, and 121-129 of SEQ ID NO: 1.

5. The method according to claim 4, wherein the immunizing polypeptide is 5 to 20 amino acid residues in length and comprises the amino acid sequence specific to the CNS tau protein.

6. The method according to claim 5, wherein the immunizing polypeptide consists of sequential amino acid residues selected from the group consisting of 121-128 of SEQ ID NO: 1, 118-131 of SEQ ID NO: 1, and 121-129 of SEQ ID NO: 1.

7. A method of detecting tauopathy in an individual suspected of having a tauopathy by determining a level of a central nervous system (CNS) tau protein in a sample obtained from the individual, said method comprising:
contacting the antibody according to claim 1 with the sample obtained from the individual suspected of tauopathy under conditions sufficient for formation of a complex between the antibody and any CNS tau protein in the sample,
detecting the complex as an indication of the level of CNS tau protein in the sample, and
determining tauopathy in the individual if an elevated level of CNS tau is detected in the sample compared to levels of CNS tau protein in samples from control patients without a tauopathy.

8. The method according to claim 7, wherein the tauopathy is Alzheimer's disease.

9. The method according to claim 7, wherein the sample has been treated by denaturation in the presence of a protein-solubilizing agent to remove concomitant proteins.

10. The method according to claim 9, wherein the sample has been further treated by condensation.

11. The method according to claim 7, wherein the sample is blood.

12. The method according to claim 7, wherein the contacting and detecting steps are performed with an enzyme-linked immunosorbent assay.

* * * * *